US008227249B2

(12) United States Patent
Calos

(10) Patent No.: US 8,227,249 B2
(45) Date of Patent: *Jul. 24, 2012

(54) METHODS AND COMPOSITIONS FOR GENOMIC MODIFICATION

(75) Inventor: Michele P. Calos, Woodside, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 963 days.

This patent is subject to a terminal disclaimer.

(21) Appl. No.: 12/061,580

(22) Filed: Apr. 2, 2008

(65) Prior Publication Data

US 2009/0035862 A1 Feb. 5, 2009

Related U.S. Application Data

(63) Continuation of application No. 10/636,290, filed on Aug. 5, 2003, now Pat. No. 7,361,641, which is a continuation of application No. 09/377,885, filed on Aug. 19, 1999, now Pat. No. 6,632,672.

(60) Provisional application No. 60/097,166, filed on Aug. 19, 1998.

(51) Int. Cl.
*C12N 15/87* (2006.01)
(52) U.S. Cl. ........................................ 435/462
(58) Field of Classification Search .................. None
See application file for complete search history.

(56) References Cited

U.S. PATENT DOCUMENTS

| 5,190,871 A | 3/1993 | Cox et al. |
| 5,470,727 A | 11/1995 | Mascarenhas et al. |
| 5,654,182 A | 8/1997 | Wahl et al. |
| 5,801,030 A | 9/1998 | McVey et al. |
| 5,830,698 A | 11/1998 | Reff et al. |
| 5,888,732 A | 3/1999 | Hartley et al. |

OTHER PUBLICATIONS

Buchholz et al., "Improved Properties of FLP Recombinase Evolved by Cycling—Mutagenesis," Nature Biotechnology 16:657-662 (1998).
Christiansen et al., "A Resolvase-Like Protein is Required for the Site-Specific Integration of the Temperate Lactococcal Bacteriophage TP901-1," Journal of Bacteriology 178(17):5164-5173 (1996).
Dorgai et al., "Identifying Determinants of Recombination Specificity: Construction and Characterization of Mutant Bacteriophage Integrases," J. Mol. Biol. 252:178-188 (1995).
Hartung et al., "CRE Mutants with Altered DNA Binding Properties," Journal of Biological Chemistry 273:22884-22891 (1998).
Matsuura et al., "The sre Gene (ORF469) Encodes a Site-Specific Recombinase Responsible for Integration of the R4 Phage Genome," Journal of Bacteriology 178(11):3374-3376 (1996).
Thorpe et al., "In Vitro Site-Specific Integration of Bacteriophage DNA Catalyzed by a Recombinase of the Resolvase/Invertase Family," Proc. Natl. Acad. Sci., U.S.A., 95:5505-5510 (1998).

Agah, et al., "Targeted Expression of Cre Recombinase Provokes Cardiac-restricted, Site-specific Rearrangement in Adult Ventricular Muscle In Vivo," J. Clin. Invest 100:169-179 (1997).
Albert et al., "Site-specific Integration of DNA into Wild-type and Mutant lox Sites Placed in the Plant Genome," Plant Journal 7(4):649-659 (1995).
Argos et al., "The Integrase Family of Site-Specific Recombinases: Regional Similarities and Global Diversity," EMBO J. 5(2):433-440 (1986).
Araki et al., "Molecular and Functional Organization of Yeast Plasmic pSR1," J. Mol. Biol. 182:191-203 (1985).
Baubonis and Sauer, "Genomic Targeting with Purified Cre Recombinase," 21(9):2025-2029 (1993).
Broach et al., "Recombination within the Yeast Plasmid 2μ Circle is Site-Specific," Cell 29:227-234 (1982).
Brondsted and Hammer, "Use of the Integration Elements Encoded by the Temperate Lactococcal Bacteriophage TP901-1 to Obtain Chromosomal Single-Copy Transcriptional Fusions in *Lactococcus lactis*," Appl. & Envirol. Microbiology 65(2):752-758 (1999).
Christiansen et al., "Characterization of the Lactococcal Temperate Phage TP901-1 and its Site-Specific Integration," *J. of Bacteriology* 176(4):1069-1076 (1994).
Christiansen et al., "A Resolvase-like Protein is Required for the Site-specific Integration of the Temperate Lactococcal Bacteriophage TP901-1," J. of Bacteriology 178(17):5164-5173 (1996).
Crellin and Rood, "The Resolvase/Invertase Domain of the Site-specific Recombinase TnpX is Functional and Recognizes a Target Sequence that Resembles the Junction of the Circular Form of the Clostridium perfringens Transposon Tn4451," J. of Bacteriology 179(16):5148-5156 (1997).
Dale and Ow, "Intra- and Intermolecular Site-specific Recombination in Plant Cells Mediated by Bacteriophage P1 Recombinase," Gene 91:79-85 (1990).
Flotte and Carter, Adeno-associated Virus Vectors for Gene Therapy, Gene Therapy 2:357-362 (1995).
Golic and Lindquist, "The FLP Recombinase of Yeast Catalyzes Site-specific Recombination of the Drosophila Genome," Cell 59:499-509 (1989).
Golic and Golic, "Engineering the Drosophila Genome: Chromosome Rearrangements by Design," Genetics 144:1693-1711 (1996).

(Continued)

*Primary Examiner* — Ileana Popa
(74) *Attorney, Agent, or Firm* — Edward J. Baba; Bozicevic, Field & Francis LLP

(57) ABSTRACT

The present invention provides methods of site-specifically integrating a polynucleotide sequence of interest in a genome of a eucaryotic cell, as well as, enzymes, polypeptides, and a variety of vector constructs useful therefore. In the method, a targeting construct comprises, for example, (i) a first recombination site and a polynucleotide sequence of interest, and (ii) a site-specific recombinase, which are introduced into the cell. The genome of the cell comprises a second recombination site. Recombination between the first and second recombination sites is facilitated by the site-specific recombinase. The invention describes compositions, vectors, and methods of use thereof, for the generation of transgenic cells, tissues, plants, and animals. The compositions, vectors, and methods of the present invention are also useful in gene therapy techniques.

8 Claims, 12 Drawing Sheets

OTHER PUBLICATIONS

Hallet and Sherratt, "Transposition and Site-specific Recombination: Adapting DNA Cut-and-paste Mechanisms to a Variety of Genetic Rearrangements," FEMA Microbiol. Rev. 21:157-178 (1997).

Huang et al., "Convenient and Reversible Site-specific Targeting of Exogenous DNA into a Bacterial Chromosome by Use of the FLP Recombinase: The FLIRT System," J. of Bacteriology 179(19):6076-6083 (1997).

Kay et al., "Gene Therapy," Proc. Natl. Acad. Sci. USA 94:12744-12746 (1997).

Kuhstoss and Rao, "Analysis of the Integration Function of the Streptomycete Bacteriophase φC31," J. Mol. Biol. 222:897-908 (1991).

Lyznik et al., "Activity of Yeast FLP Recombinase in Maize and Rice Protoplasts," Nucleic Acids Res. 21(4):969-975 (1993).

Matsuura et al., "The sre Gene (ORF469) Encodes a Site-specific Recombinase Responsible for Integration of the R4 Phage Genome," J. of Bact. 178(11):3374-3376 (1996).

Matsuzaki et al., "Chromosome Engineering in *Saccharomyces cerevisiae* by Using a Site-specific Recombination System of a Yeast Plasmid," J. of Bacteriology 172(2):610-618 (1990).

Muzyczka, "Use of Adeno-associated Virus as a General Transduction Vector for Mammalian Cells," Curr. Topics Microbiol. Immunol. 158:97-129 (1992).

Odell et al., "Site-directed Recombination in the Genome of Transgenic Tobacco," Mol. Gen. Genet. 223:369-378 (1990).

Rausch and Lehmann, "Structural Analysis of the Actinophage φC31 attachment," Nucl. Acids Res. 19 (19):5187-5189 (1991).

Sauer, "Multiplex Cre/Lox Recombination Permits Selective Site-specific DNA Targeting to Both a Natural and an Engineered Site in the Yeast Genome," Nucl. Acids Res. 24(23):4608-4613 (1996).

Sauer, "Functional Expression of the cre-lox Site-specific Recombination System in the Yeast *Saccharomyces cerevisiae*", Mol. Cell. Biol. 7(6):2087-2096 (1987).

Sauer, "Identification of Cryptic lox Sites in the Yeast Genome by Selection for Cre-mediated Chromosome Translocations that Confer Multiple Drug Resistance," J. Mol. Biol. 223:911-928 (1992).

Sauer and Henderson, "Targeted Insertion of Exogenous DNA into the Eukaryotic Genome by the Cre Recombinase," New Biologist 2:441-449 (1990).

Shirai et al., "Site-specific Integration of the Actinophage R4 Genome into the Chromosome of *Streptomyces parvulus* Upon Lysogenization," J. of Bacteriology 173(13):4237-4239 (1991).

Sternberg and Hamilton, "Bacteriophage P1 Site-specific Recombination, I. Recombination Between loxP Sites," J. Mol. Biol. 150:467-486 (1981).

Sternberg et al., "Bacteriophage P1 Site-specific Recombination II, Recombination Between loxP and the Bacterial Chromosome," J. Mol. Biol. 150:487-507 (1981).

Sternberg, "Bacteriophage P1 cre Gene and its Regulatory Region, Evidence for Multiple Promoters and for Regulation by DNA Methylation," J. Mol. Biol. 187:197-212 (1986).

Thorpe and Smith, "In Vitro Site-specific Integration of Bacteriophage DNA Catalyzed by a Recombinase of the Resolvase/Invertase Family," PNAS USA 95:5505-5510 (1998).

Van Deursen et al., "Cre-mediated Site-specific Translocation Between Nonhomologous Mouse Chromosomes," Natl. Acad. Sci. USA 92:7376-7380 (1995).

Verma and Somia, "Gene Therapy—Promises, Problems and Prospects," Nature 389:239-242 (1997).

WTLoxP     ATAACTTCGTATA ATGTATGC TATACGAAGTTAT    (SEQ ID NO: 20)

ψLoxh7q21  ATACATACGTATA TATGTATA TATACATATAT     (SEQ ID NO: 21)

ψCoreh7q21 ATAACTTCGTATA TATGTATA TATACGAAGTTAT   (SEQ ID NO: 22)

FIG. 1D

| p220K | | | |
|---|---|---|---|
| | Blues / Total | % Integration | Corrected % Integration |
| no DNA | 0/7,970 | < .01% | < .08% |
| pCMVInt only | 0/13,600 | < .007% | < .04% |
| pTSAD only | 1/11,830 | 0.008% | 0.05% |
| pCMVInt + pTSAD | 3/32,680 | 0.009% | 0.06% |

| p220KattB35 | | | |
|---|---|---|---|
| | Blues / Total | % Integration | Corrected % Integration |
| no DNA | 0/64,530 | < .002% | < .01% |
| pCMVInt only | 0/42,720 | < .002% | < .02% |
| pTSAD only | 0/39,930 | < .003% | < .02% |
| pCMVInt + pTSAD | 382/157,710 | 0.242% | 1.69% |

| p220KattBfull | | | |
|---|---|---|---|
| | Blues / Total | % Integration | Corrected % Integration |
| no DNA | 0/70,350 | < .001% | < .01% |
| pCMVInt only | 0/41,960 | < .002% | < .02% |
| pTSAD only | 0/39,740 | < .003% | < .02% |
| pCMVInt + pTSAD | 1,799/ 166,890 | 1.08% | 7.50% |

FIG. 7

Wild-type loxP (SEQ ID NO: 20) ATAACTTCGTATA ATGTATGC TATACGAAGTTAT

| | | | | (LAB DESIGNATION) | Accession number | Location/gene |
|---|---|---|---|---|---|---|
| Human | | | | | | |
| (SEQ ID NO: 23) | ACAACCATTTATA | ATATATAA | TATATGATGTTAT | PSTR1 | HSAC002082 | Xp22 |
| (SEQ ID NO: 24) | ATACATACGTATA | TATGTATA | TATACATATAT | P2 | AC002383 | 7q21 |
| (SEQ ID NO: 25) | ATATACACGTATA | TATATATA | TATACGTATATAT | P4 | Z98048 | 22q13 |
| (SEQ ID NO: 26) | CAAACAAGGTATA | TGCCTGTA | TATACGAAATGGT | P3 | AC003081 | 7q31 |
| (SEQ ID NO: 27) | ATATATACGTATA | TATACATA | TATACGTATATAT | Bh1 | AC002090 | 17 |
| (SEQ ID NO: 28) | ATATATACGTATA | TATACATA | TATACACATATAT | Bh3 | HS107N3 | |
| (SEQ ID NO: 29) | ATAAATATGTATA | TGTATATG | TATACGTATATAA | Bh4 | HSAC000112 | |
| (SEQ ID NO: 30) | ATATATATGTATA | TGTATATG | TATACGTATATAT | Bh5 | HSCU90B3 | |
| (SEQ ID NO: 31) | ATATATACGTATA | TACACATA | TATACGTATATAC | Bh7 | HSXIST1 | Xq13 |
| Mouse | | | | | | |
| (SEQ ID NO: 32) | ATATTGACATATA | TTATAAAG | TATAAGTAGTTAT | MO1 | MMU28404 | 9 MIP1 |
| (SEQ ID NO: 33) | GTAACTGAGTATA | TGCATATA | TATACGTATATAT | MO2 | AF033025 | 5 MDR1 |
| (SEQ ID NO: 34) | ATAACATATATA | TTTATATA | TATATATATTTAA | Bm1 | AC000399 | 9 |
| (SEQ ID NO: 35) | ATATATATGTATA | TATATACA | TATACATACATAT | Bm2 | MMBGCXD | β-globin |
| (SEQ ID NO: 36) | AGCACTTCCTATA | TAACTTCA | TATACGTAGCTCC | Bm3 | MMU48804 | PW1 |

FIG. 8A

| | | (LAB DESIGNATION) | Accession number | Location/gene |
|---|---|---|---|---|
| Invertebrate | | | | |
| | *Caenorhabditis elegans* | | | |
| (SEQ ID NO: 37) | ATAGCGTCGTATA ATCCGAAA TATACAGATCTAT | Bi1 | CEC47E12 | |
| Plant and Fungus | | | | |
| | *Arabidopsis thaliana* | | | |
| (SEQ ID NO: 38) | CTAGTTTGGTATA TATATATA TATACTAATTTAT | Bp1 | ATF28A23 | |
| (SEQ ID NO: 39) | ATAACTTTGTATA GTTTAACT TATATTAGGTACT | Bp3 | IG002P16 | |
| | *Flaveria anomala* | | | |
| (SEQ ID NO: 40) | ATCAGTTAGTATA TATTCGTA TATACGTAGATAT | Bp2 | FAGDCSH | |
| | *Saccharomyces cerevisiae* | | | |
| (SEQ ID NO: 41) | TTGCCTTCGTATA TACCTTTC TATACCAAGTAAT | By1 | SCFAS1 | |

FIG. 8B

SEQUENCE LISTING

<160> NUMBER OF SEQ ID NOS: 41

<210> SEQ ID NO 1
<211> LENGTH: 34
<212> TYPE: DNA
<213> ORGANISM: Bacteriophage P1

<400> SEQUENCE: 1
ataacttcgt atagcataca ttatacgaag ttat                                    34

<210> SEQ ID NO 2
<211> LENGTH: 34
<212> TYPE: DNA
<213> ORGANISM: Saccharomyces cerevisiae

<400> SEQUENCE: 2
gaagttccta tacttctaga agaataggaa cttc                                    34

<210> SEQ ID NO 3
<211> LENGTH: 12
<212> TYPE: DNA
<213> ORGANISM: phage R4

<400> SEQUENCE: 3
gaagcagtgg ta                                                                12

<210> SEQ ID NO 4
<211> LENGTH: 34
<212> TYPE: DNA
<213> ORGANISM: Artificial Sequence
<220> FEATURE:
<223> OTHER INFORMATION: loxP search pattern
<221> NAME/KEY: misc_feature
<222> LOCATION: (1)...(34)
<223> OTHER INFORMATION: n = A,T,C or G

<400> SEQUENCE: 4
ataacttcgt atannnnnnn ntatacgaag ttat                                    34

<210> SEQ ID NO 5
<211> LENGTH: 34
<212> TYPE: DNA
<213> ORGANISM: Artificial Sequence
<220> FEATURE:
<223> OTHER INFORMATION: loxP search pattern 2
<221> NAME/KEY: misc_feature
<222> LOCATION: (1)...(34)
<223> OTHER INFORMATION: n = A,T,C or G

<400> SEQUENCE: 5
atnacnncnt atannntann ntatangnng tnat                                    34

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 6
gaactagtcg tagggtcgcc gacatgacac                                              30

<210> SEQ ID NO 7
<211> LENGTH: 30
<212> TYPE: DNA

```
<213> ORGANISM: Artificial Sequence
<220> FEATURE:
<223> OTHER INFORMATION: Description of Artificial Sequence: primer

<400> SEQUENCE: 7
gtggatccgg gtgtctcgct acgccgctac                                    30

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: linker

<400> SEQUENCE: 8
gctcggccaa aaaggcctgc a                                             21

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: linker

<400> SEQUENCE: 9 ggccttttg gccg                                                      14

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
caggtaccgt cgacgatgta ggtcacggtc                                    30

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 11
gtcgacatgc ccgccgtgac cg                                            22

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 12
cgactagtac tgacggacac accgaa                                        26

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 13
gtactagtcg cgctcgcgcg actgacg                                       27
```

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: linker

<400> SEQUENCE: 14
catgaggcca aaaaggcctg ca                                              22

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: linker

<400> SEQUENCE: 15 ggccttttg gcct                                                        14

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: p220KattB35
      first oligonucleotide

<400> SEQUENCE: 16
gatccgatat cgcgcccggg gagcccaagg gcacgccctg gcaccg                    46

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: p220KattB35
      second oligonucleotide

<400> SEQUENCE: 17
tcgacggtgc cagggcgtgc ccttgggctc cccgggcgcg atatcg                    46

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: multiple
      cloning site first oligonucleotide

<400> SEQUENCE: 18
aattaccgcg gggcgcgccg tttaaacgca tgccaattgg gccggccg                  48

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: multiple
      cloning site second oligonucleotide

<400> SEQUENCE: 19
aattcggccg gcccaattgg catgcgttta aacggcgcgc ccgcggt                   48

<210> SEQ ID NO 20
<211> LENGTH: 34
<212> TYPE: DNA

```
<213> ORGANISM: Artificial Sequence
<220> FEATURE:
<223> OTHER INFORMATION: Description of Artificial Sequence: wild-type
      loxP site

<400> SEQUENCE: 20
ataacttcgt ataatgtatg ctatacgaag ttat                                 34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: "psi"
      loxh7q21

<400> SEQUENCE: 21
atacatacgt atatatgtat atatacatat atat                                 34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: "psi"
      coreh7q21

<400> SEQUENCE: 22
ataacttcgt atatatgtat atatacgaag ttat                                 34

<210> SEQ ID NO 23
<211> LENGTH: 34
<212> TYPE: DNA
<213> ORGANISM: Homo sapiens

<400> SEQUENCE: 23
acaaccattt ataatatata atatatgatg ttat                                 34

<210> SEQ ID NO 24
<211> LENGTH: 34
<212> TYPE: DNA
<213> ORGANISM: Homo sapiens

<400> SEQUENCE: 24
atacatacgt atatatgtat atatacatat atat                                 34

<210> SEQ ID NO 25
<211> LENGTH: 34
<212> TYPE: DNA
<213> ORGANISM: Homo sapiens

<400> SEQUENCE: 25
atatacacgt atatatatat atacgtat atat                                   34

<210> SEQ ID NO 26
<211> LENGTH: 34
<212> TYPE: DNA
<213> ORGANISM: Homo sapiens

<400> SEQUENCE: 26
caaacaaggt atatgcctgt atatacgaaa tggt                                 34

<210> SEQ ID NO 27
<211> LENGTH: 34
<212> TYPE: DNA
<213> ORGANISM: Homo sapiens
```

```
<400> SEQUENCE: 27
atatatacgt atatatacat atatacgtat atat                    34

<210> SEQ ID NO 28
<211> LENGTH: 34
<212> TYPE: DNA
<213> ORGANISM: Homo sapiens

<400> SEQUENCE: 28
atatatacgt atatatacat atatacacat atat                    34

<210> SEQ ID NO 29
<211> LENGTH: 34
<212> TYPE: DNA
<213> ORGANISM: Homo sapiens

<400> SEQUENCE: 29
ataaatatgt atatgtatat gtatacgtat ataa                    34

<210> SEQ ID NO 30
<211> LENGTH: 34
<212> TYPE: DNA
<213> ORGANISM: Homo sapiens

<400> SEQUENCE: 30
atatatatgt atatgtatat gtatacgtat atat                    34

<210> SEQ ID NO 31
<211> LENGTH: 34
<212> TYPE: DNA
<213> ORGANISM: Homo sapiens

<400> SEQUENCE: 31
atatatacgt atatacacat atatacgtat atac                    34

<210> SEQ ID NO 32
<211> LENGTH: 34
<212> TYPE: DNA
<213> ORGANISM: Mus sp.

<400> SEQUENCE: 32
atattgacat atattataaa gtataagtag ttat                    34

<210> SEQ ID NO 33
<211> LENGTH: 34
<212> TYPE: DNA
<213> ORGANISM: Mus sp.

<400> SEQUENCE: 33
gtaactgagt atatgcatat atatacgtat atat                    34

<210> SEQ ID NO 34
<211> LENGTH: 34
<212> TYPE: DNA
<213> ORGANISM: Mus sp.

<400> SEQUENCE: 34
ataacatatt atatttatat atatatatat ttaa                    34

<210> SEQ ID NO 35
<211> LENGTH: 34
<212> TYPE: DNA
<213> ORGANISM: Mus sp.
```

```
<400> SEQUENCE: 35
atatatatgt atatatatac atatacatac atat                               34

<210> SEQ ID NO 36
<211> LENGTH: 34
<212> TYPE: DNA
<213> ORGANISM: Mus sp.

<400> SEQUENCE: 36
agcacttcct atataacttc atatacgtag ctcc                               34

<210> SEQ ID NO 37
<211> LENGTH: 34
<212> TYPE: DNA
<213> ORGANISM: Caenorhabditis elegans

<400> SEQUENCE: 37
atagcgtcgt ataatccgaa atatacagat ctat                               34

<210> SEQ ID NO 38
<211> LENGTH: 34
<212> TYPE: DNA
<213> ORGANISM: Arabidopsis thaliana

<400> SEQUENCE: 38
ctagtttggt atatatatat atatactaat ttat                               34

<210> SEQ ID NO 39
<211> LENGTH: 34
<212> TYPE: DNA
<213> ORGANISM: Arabidopsis thaliana

<400> SEQUENCE: 39
ataactttgt atagtttaac ttatattagg tact                               34

<210> SEQ ID NO 40
<211> LENGTH: 34
<212> TYPE: DNA
<213> ORGANISM: Flaveria anomala

<400> SEQUENCE: 40
atcagttagt atatattcgt atatacgtag atat                               34

<210> SEQ ID NO 41
<211> LENGTH: 34
<212> TYPE: DNA
<213> ORGANISM: Saccharomyces cerevisiae

<400> SEQUENCE: 41
ttgccttcgt atatacctttt ctataccaag taat                              34
```

METHODS AND COMPOSITIONS FOR GENOMIC MODIFICATION

CROSS-REFERENCE TO RELATED APPLICATIONS

This application is related to U.S. Provisional Patent Application Ser. No. 60/097,166, filed Aug. 19, 1998, from which priority is claimed under 35 U.S.C. §119(e)(1), and which application is incorporated herein by reference in its entirety. This application is a continuation of U.S. patent application Ser. No. 09/377,885, now issued as U.S. Pat. No. 6,632,672, filed Aug. 19, 1999, from which priority is claimed under 35 U.S.C. §120, and which application is incorporated herein by reference in its entirety. This application is also a continuation of U.S. patent application Ser. No. 10/636,290, now issued as U.S. Pat. No. 7,361,641, filed Aug. 5, 2003, from which priority is claimed under 35 U.S.C. §120, and which application is incorporated herein by reference in its entirety.

FEDERALLY-SPONSORED RESEARCH OR DEVELOPMENT

This invention was made with Government support under contracts DK051834 and DK055569 awarded by the National Institutes of Health. The Government has certain rights in this invention.

FIELD OF THE INVENTION

The present invention relates to the field of biotechnology, and more specifically to the field of genomic modification. Disclosed herein are compositions, vectors, and methods of use thereof, for the generation of transgenic cells, tissues, plants, and animals. The compositions, vectors, and methods of the present invention are also useful in gene therapy techniques.

BACKGROUND OF THE INVENTION

Permanent genomic modification has been a long sought after goal since the discovery that many human disorders are the result of genetic mutations that could, in theory, be corrected by providing the patient with a non-mutated gene. Permanent alterations of the genomes of cells and tissues would also be valuable for research applications, commercial products, protein production, and medical applications. Furthermore, genomic modification in the form of transgenic animals and plants has become an important approach for the analysis of gene function, the development of disease models, and the design of economically important animals and crops.

A major problem with many genomic modification methods associated with gene therapy is their lack of permanence. Life-long expression of the introduced gene is required for correction of genetic diseases. Indeed, sustained gene expression is required in most applications, yet current methods often rely on vectors that provide only a limited duration of gene expression. For example, gene expression is often curtailed by shut-off of integrated retroviruses, destruction of adenovirus-infected cells by the immune system, and degradation of introduced plasmid DNA (Anderson, W F, Nature 329:25-30, 1998; Kay, et al, Proc. Natl. Acad. Sci. USA 94:12744-12746, 1997; Verma and Somia, Nature 389:239-242, 1997). Even in shorter-term applications, such as therapy designed to kill tumor cells or discourage regrowth of endothelial tissue after restenosis surgery, the short lifetime of gene expression of current methods often limits the usefulness of the technique.

One method for creating permanent genomic modification is to employ a strategy whereby the introduced DNA becomes part of (i.e., integrated into) the existing chromosomes. Of existing methods, only retroviruses provide for efficient integration. Retroviral integration is random, however, thus the added gene sequences can integrate in the middle of another gene, or into a region in which the added gene sequence is inactive. In addition, a different insertion is created in each target cell. This situation creates safety concerns and produces an undesirable loss of control over the procedure.

Adeno-associated virus (AAV) often integrates at a specific region in the human genome. However, vectors derived from AAV do not integrate site-specifically due to deletion of the toxic rep gene (Flotte and Carter, Gene Therapy 2:357-362, 1995; Muzyczk, Curr. Topics Microbiol. Immunol. 158:97-129, 1992). The small percentage of the AAV vector population that eventually integrates does so randomly. Other methods for genomic modification include transfection of DNA using calcium phosphate co-precipitation, electroporation, lipofection, microinjection, protoplast fusion, particle bombardment, or the Ti plasmid (for plants). All of these methods produce random integration at low frequency. Homologous recombination produces site-specific integration, but the frequency of such integration is very low.

Another method that has been considered for the integration of heterologous nucleic acid fragments into a chromosome is the use of a site-specific recombinase (an example using Cre is described below). Site-specific recombinases catalyze the insertion or excision of nucleic acid fragments. These enzymes recognize relatively short, unique nucleic acid sequences that serve for both recognition and recombination. Examples include Cre (Sternberg and Hamilton, J Mol Biol 150:467-486, 1981), Flp (Broach, et al, cell-29:227-234, 1982) and R (Matsuzaki, et al, J Bacteriology 172:610-618, 1990).

One of the most widely studied site-specific recombinases is the enzyme Cre from the bacteriophage P1. Cre recombines DNA at a 34 basepair sequence called loxP, which consists of two thirteen basepair palindromic sequences flanking an eight basepair core sequence. Cre can direct site-specific integration of a loxP-containing targeting vector to a chromosomally placed loxP target in both yeast and mammalian cells (Sauer and Henderson, New Biol 2:441-449, 1990). Use of this strategy for genomic modification, however, requires that a chromosome first be modified to contain a loxP site (because this sequence is not known to occur naturally in any organism but P1 bacteriophage), a procedure which suffers from low frequency and unpredictability as discussed above. Furthermore, the net integration frequency is low due to the competing excision reaction also mediated by Cre. Similar concerns arise in the conventional use of other, well-known, site-specific recombinases.

A need still exists, therefore, for a convenient means by which chromosomes can be permanently modified in a site-specific manner. The present invention addresses that need.

BRIEF DESCRIPTION OF THE INVENTION

Accordingly, in one embodiment, the present invention is directed to a method of site-specifically integrating a polynucleotide sequence of interest in a genome of a eucaryotic cell. The method comprises introducing (i) a circular targeting constructs comprising a first recombination site and the polynucleotide sequence of interest, and (ii) a site-specific recombinase into the eucaryotic cell, wherein the genome of the cell comprises a second recombination site native to the genome and recombination between the first and second recombination sites is facilitated by the site-specific recombinase. The cell is maintained under conditions that allow recombination between the first and second recombination sites and the recombination is mediated by the site-specific recombinase. The result of the recombination is site-specific integration of the polynucleotide sequence of interest in the genome of the eucaryotic cell.

The recombinase may be introduced into the cell before, concurrently with, or after introducing the circular targeting construct. Further, the circular targeting construct may comprise other useful components, such as a bacterial origin of replication and/or a selectable marker.

In certain embodiments, the recombinase may facilitate recombination between two sites designated recombinase-mediated-recombination sites (RMRS) and the RMRS comprises a first DNA sequence (RMRS5'), a core region A, and a second DNA sequence (RMRS3') in the relative order RMRS5'-core region A-RMRS3'. In this embodiment, for example, RMRS may be a loxP site or a FRT site and the recombinase may be Cre and FLP, respectively.

In additional embodiments, (i) the second recombination site is a pseudo-RMRS site, and the second recombination site comprises a first DNA sequence (attT5'), a core region B, and a second DNA sequence (attT3') in the relative order attT5'-core region B-attT3', and (ii) the first recombination site is a hybrid-recombination site comprising RMRS5'-core region B-RMRS3' or attT5'-core region B-attT3'.

In yet further embodiments, the site-specific recombinase is a recombinase encoded by a phage selected from the group consisting of φC31, TP901-1, and R4. The recombinase may facilitate recombination between a bacterial genomic recombination site (attB) and a phage genomic recombination site (attP), and (i) the second recombination site may comprise a pseudo-attP site, and (ii) the first recombination site may comprise the attB site or (i) the second recombination site may comprise a pseudo-attB site, and (ii) the first recombination site may comprise the attP site.

In another embodiment, (i) attB comprises a first DNA sequence (attB5'), a bacterial core region, and a second DNA sequence (attB3') in the relative order attB5'-bacterial core region-attB3', (ii) attP comprises a first DNA sequence (attP5'), a phage core region, and a second DNA sequence (attP3') in the relative order attP5'-phage core region-attP3', and (iii) wherein the recombinase mediates production of recombination-product sites that can no longer act as a substrate for the recombinase, the recombination-product sites comprising the relative order attB5'-recombination-product site-attP3' and attP5'-recombination-product site-attB3'.

In particularly preferred embodiments, (i) the second recombination site is a pseudo-attP site, the second recombination site comprises a first DNA sequence (attT5'), a core region B, and a second DNA sequence (attT3') in the relative order attT5'-core region B-attT3', (ii) the first recombination site is an attB site comprising attB5'-bacterial core region-attB3', and (iii) wherein the recombinase mediates production of recombination-product sites that can no longer act as a substrate for the recombinase, the recombination-product sites comprising the relative order attT5'-recombination-product site-attB3' {polynucleotide of interest}attB5'-recombination-product site-attT3'. Alternatively, (i) the second recombination site is a pseudo-attB site, and the second recombination site comprises a first DNA sequence (attT5'), a core region B, and a second DNA sequence (attT3') in the relative order attT5'-core region B-attT3', (ii) the first recombination site is an attP site comprising attP5'-bacterial core region-attP3', and (iii) wherein the recombinase mediates production of recombination-product sites that can no longer act as a substrate for the recombinase, the recombination-product sites comprising the relative order attT5'-recombination-product site-attP3' {polynucleotide of interest}attP5'-recombination-product site-attT 3'.

In yet further embodiments, the site-specific recombinase is introduced into the cell as a polypeptide. In alternative embodiments, the site-specific recombinase in introduced into the cell as a polynucleotide encoding the recombinase and an expression cassette, optionally carried on a transient expression vector, comprises the polynucleotide encoding the recombinase.

In another embodiment, the invention is directed to a vector for site-specific integration of a polynucleotide sequence into the genome of a eucaryotic cell. The vector comprises (i) a circular backbone vector, (ii) a polynucleotide of interest operably linked to a eucaryotic promoter, and (iii) a first recombination site, wherein the genome of the cell comprises a second recombination site native to the genome and recombination between the first and second recombination sites is facilitated by a site-specific recombinase.

In certain embodiments, the recombinase normally facilitates recombination between a bacterial genomic recombination site (attB) and a phage genomic recombination site (attP) and the first recombination site may be either attB or attP.

In still another embodiment, the invention is directed to a kit for site-specific integration of a polynucleotide sequence into the genome of a eucaryotic cell The kit comprises, (i) a vector as described above and (ii) a site-specific recombinase.

In another embodiment, the invention is directed to a eucaryotic cell having a modified genome. The modified genome comprises an integrated polynucleotide sequence of interest whose integration was mediated by a recombinase and wherein the integration was into a recombination site native to the eucaryotic cell genome and the integration created a recombination-product site comprising the polynucleotide sequence.

In certain embodiments, the recombination-site product comprises the components attT5'-recombination-product site-attB3' and attB5'-recombination-product site-attT3', wherein (i) the native recombination site is a pseudo-attP site, and the native recombination site comprises a first DNA sequence (attT5'), a core region B, and a second DNA sequence (attT3') in the relative order attT5'-core region B-attT3', (ii) the integrated polynucleotide sequence comprises a first recombination site comprising an attB site comprising attB5'-bacterial core region-attB3', and (iii) wherein the recombinase mediates production of recombination-product sites that can no longer act as a substrate for the recombinase, the recombination-product sites comprising the relative order attT5'-recombination-product site-attB3' {polynucleotide of interest}attB5'-recombination-product site-attT3'. Alternatively, the recombination-site product comprises the components attT5'-recombination-product site-attB3' and attB5'-recombination-product site-attT3', wherein (i) the native recombination site is a pseudo-attB site, and the native recombination site comprises a first DNA sequence (attT5'), a core region B, and a second DNA sequence (attT3') in the relative order attT5'-core region B-attT3', (ii) the integrated polynucleotide sequence comprises a first recombination site comprising an attP site comprising attP5'-phage core region-attP3', and (iii) wherein the recombinase mediates production of recombination-product sites that can no longer act as a substrate for the recombinase, the recombination-product sites comprising the relative order attT5'-recombination-product site-attP3'{polynucleotide of interest}attP5'-recombination-product site-attT3'.

In further embodiments, the subject invention is directed to transgenic plants and animals comprising at least one cell as described above, as well as methods of producing the same.

In yet other embodiments, the invention is directed to methods of treating a disorder in a subject in need of such treatment. The method comprises site-specifically integrating a polynucleotide sequence of interest in a genome of at least one cell of the subject, wherein the polynucleotide facilitates production of a product that treats the disorder in the subject. The site-specific integration may be carried out in vivo in the subject, or ex vivo in cells and the cells are then introduced into the subject.

A further embodiment of the invention comprises cells, tissues, transgenic animals and/or plants whose genomes have been modified using the methods described herein.

In another aspect, the present invention provides a method of modifying a genome of a cell. In the method, an attB or an attP recombination site is into the genome of a cell, wherein (i) the recombination site is recognized by a recombinase, and (ii) the cell normally does not comprise the attB or attP site. The vectors described herein and above are useful in the practice of this aspect of the invention. In a preferred embodiment, the cell that is being modified is a eucaryotic cell.

In yet another aspect, the present invention provides expression cassettes, comprising a polynucleotide encoding a site-specific recombinase, wherein (i) the recombinase is encoded by a phage (typically selected from the group consisting of φC31, TP901-1, and R4) and the recombinase is operably linked to a eucaryotic promoter. The vectors described herein and above are useful in the practice of this aspect of the invention.

These and other embodiments of the present invention will readily occur to those of ordinary skill in the art in view of the disclosure herein.

BRIEF DESCRIPTION OF THE FIGURES

FIG. 1A shows an unmodified plasmid containing a gene for ampicillin resistance and a gene for β-galactosidase expression (lacz) under control of the CMV promoter (pLCG1). FIG. 1B shows the same plasmid with wild-type loxP sequences flanking the lacZ gene (pWTLox²). FIG. 1C shows the plasmid with the ψlox h7q21 pseudo-lox recombination sequence on one side of lacz and a lox sequence with wild-type palindromes and a pseudo-lox core on the other side (pψloxh7q21).

FIG. 1D shows the DNA sequences of the lox sites from pWTLox² (top line of FIG. 1D) and plasmid pψloxh7q21 (bottom lines of FIG. 1D).

FIG. 4A shows plasmid pInt, for expression of φC31 integrase in E. coli; FIG. 4B depicts plasmid pCMVInt for expression of integrase in mammalian cells; FIG. 4C depicts plasmid pBCPB+, an intramolecular integration assay vector; FIG. 4D shows plasmid p220KattBfull, an EBV vector bearing attB, the target for integration events; FIG. 4E shows plasmid pTSAD, the donor for integration events, bearing attP. $Kan^R$, $Amp^R$, $Chlor^R$ and $Hyg^R$ are genes for resistance to kanamycin, ampicillin, chloramphenicol, and hygromycin, respectively.

FIG. 7 shows the results of a bimolecular integration assay performed in human cells as described in the examples. Results are shown for human cells carrying three EBV plasmids, p220K, a negative control lacking attB; p220KattB35, which carries the minimally sized attB; and p220KattBfull, carrying the full-sized attB. Integration frequencies are shown for experiments when no DNA was transfected, when either the integrase expression plasmid pCMVInt or the attP-bearing plasmid pTSAD alone was transfected, or when both pCMVInt and pTSAD together were transfected. Only the latter conditions, in the presence of a plasmid bearing attB, lead to integration events. Integration frequencies were corrected for transfection frequency to give the accurate corrected integration frequencies in the last column. p220KattBfull produced the highest integration frequency at 7.5%.

FIGS. 8A through 8B show pseudo-loxP sequences identified by computer search, as described in the Examples. The core sequences are shown in boldface type.

DETAILED DESCRIPTION OF THE INVENTION

Figure 1C:
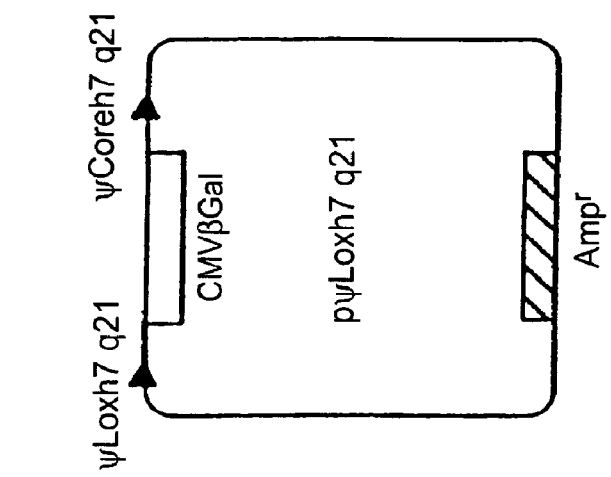
FIGS. 1A through 1C are schematics of representative plasmids useful in evaluating the efficiency of pseudo-lox recombination sequences.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J, McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

Definitions

"Recombinase" as used herein refers to a group of enzymes that can facilitate site specific recombination between defined sites, where the sites are physically separated on a single DNA molecule or where the sites reside on separate DNA molecules. The DNA sequences of the defined recombination sites are not necessarily identical. Within this group are several subfamilies including "Integrase" (including, for example, Cre and λ integrase) and "Resolvase/Invertase" (including, for example, φC31 integrase, R4 integrase, and TP-901 integrase).

By "wild-type recombination site (RS/WT)" is meant a recombination site normally used by an integrase or recombinase. For example, λ is a temperate bacteriophage that infects E. coli. The phage has one attachment site for recombination (attP) and the E. coli bacterial genome has an attachment site for recombination (attB). Both of these sites are wild-type recombination sites for λ integrase. In the context of the present invention, wild-type recombination sites occur in the homologous phage/bacteria system. Accordingly, wild-type recombination sites can be derived from the homologous system and associated with heterologous sequences, for example, the $Att_B$ site can be placed in other systems to act as a substrate for the integrase.

By "pseudo-recombination site (RS/P)" is meant a site at which recombinase can facilitate recombination even though the site may not have a sequence identical to the sequence of its wild-type recombination site. A pseudo-recombination site is typically found in an organism heterologous to the native phage/bacterial system. For example, a φC31 integrase and vector carrying a φC31 wild-type recombination site can be placed into a eucaryotic cell. The wild-type recombination sequence aligns itself with a sequence in the eucaryotic cell genome and the integrase facilitates a recombination event. When the sequence from the genomic site, in the eucaryotic cell, where the integration of the vector took place (via a recombination event between the wild-type recombination site in the vector and the genome) is examined, the sequence at the genomic site typically has some identity to but may not be identical with the wild-type bacterial genome recombination site. The recombination site in the eucaryotic cell is considered to be a pseudo-recombination site at least because the eucaryotic cell is heterologous to the normal phage/bacterial cell system. The size of the pseudo-recombination site can be determined through the use of a variety of methods including, but not limited to, (i) sequence alignment comparisons, (ii) secondary structural comparisons, (iii) deletion or point mutation analysis to find the functional limits of the pseudo-recombination site, and (iv) combinations of the foregoing. Pseudo-recombination sites typically occur naturally in the genomes of eucaryotic cells (i.e., the sites are native to the genome) and are functionally identified as described herein (e.g., see Examples).

By "hybrid-recombination site (RS/H)" as used herein refers to a recombination site constructed from portions of wild-type and/or pseudo-recombination sites. As an example, a wild-type recombination site may have a short, core region flanked by palindromes. In one embodiment of a "hybrid-recombination site" the short, core region sequence of the hybrid-recombination site matches a core sequence of a pseudo-recombination site and the palindromes of the hybrid-recombination site match the wild-type recombination site. In an alternative embodiment, the hybrid-recombination site may be comprised of flanking sites derived from a pseudo-recombination site and a core region derived from a wild-type recombination site. Other combinations of such hybrid-recombination sites will be evident to those having ordinary skill in the art, in view of the teachings of the present specification.

A recombination site "native" to the genome, as used herein, means a recombination site that occurs naturally in the genome of a cell (i.e., the sites are not introduced into the genome, for example, by recombinant means.)

By "nucleic acid construct" it is meant a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

By "nucleic acid fragment of interest" it is meant any nucleic acid fragment that one wishes to insert into a genome. Suitable examples of nucleic acid fragments of interest include therapeutic genes, marker genes, control regions, trait-producing fragments, and the like.

"Therapeutic genes" are those nucleic acid sequences which encode molecules that provide some therapeutic benefit to the host, including proteins, functional RNAs (antisense, hammerhead ribozymes), and the like. One well known example is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease, or effect a cure if the gene transfer was permanent.

Other disorders resulting from mutations in a single gene (known as monogenic disorders) include alpha-1-antitrypsin deficiency, chromic granulomatous disease, familial hypercholesterolemia, Fanconi anemia, Gaucher disease, Hunter syndrome, ornithine transcarbamylase deficiency, purine nucleoside phosphorylase deficiency, severe combined immunodeficiency disease (SCID)-ADA, X-linked SCID, hemophilia, and the like.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer.

A nucleic acid fragment of interest may additionally be a "marker nucleic acid" or "marker polypeptide". Marker genes encode proteins which can be easily detected in transformed cells and are, therefore, useful in the study of those cells Marker genes are being used in bone marrow transplantation studies, for example, to investigate the biology of marrow reconstitution and the mechanism of relapse in patients. Examples of suitable marker genes include beta-galactosidase, green or yellow fluorescent proteins, chloramphenicol acetyl transferase, luciferase, and the like.

A nucleic acid fragment of interest may additionally be a control region. The term "control region" or "control element" includes all nucleic acid components which are operably linked to a DNA fragment and involved in the expression of a protein or RNA therefrom. An operable linkage is a linkage in which the regulatory DNA fragments and the DNA sought to be expressed are connected in such a way as to permit coding sequence (the nucleic acids encoding the amino acid sequence of a protein) expression. The precise nature of the regulatory regions needed for coding sequence expression may vary from organism to organism, but will in general include a promoter region that, in prokaryotes, contains both the promoter (which directs the initiation of RNA transcription) as well as the DNA that, when transcribed into RNA, will signal synthesis initiation. Such regions will normally include those 5' noncoding sequences involved with initiation of transcription and translation, such as the enhancer, TATA box, capping sequence, CAAT sequence, and the like.

Under some circumstances, the native genome sought to be modified contains a functional coding sequence but lacks the ability to control the expression of the sequence. In such cases it would be of benefit to modify the genome by the insertion of control region(s). Such sequences include any sequence that functions to modulate-replication, transcriptional or translational regulation, and the like. Examples include promoters, signal sequences, propeptide sequences, transcription terminators, polyadenylation sequences, enhancer sequences, attenuatory sequences, intron splice site sequences, and the like.

A nucleic acid fragment of interest may additionally be a trait-producing sequence, by which it is meant a sequence conferring some non-native trait upon the organism or cell in which the protein encoded by the trait-producing sequence is expressed. The term "non-native" when used in the context of a trait-producing sequence means that the trait produced is different than one would find in an unmodified organism which can mean that the organism produces high amounts of a natural substance in comparison to an unmodified organism, or produces a non-natural substance. For example, the genome of a crop plant, such as corn, can be modified to produce higher amounts of an essential amino acid, thus creating a plant of higher nutritional quality, or could be modified to produce proteins not normally produced in plants, such as antibodies. (See U.S. Pat. No. 5,202,422 (issued Apr. 13, 1993); U.S. Pat. No. 5,639,947 (Jun. 17, 1997).) Likewise, the genome of industrially important microorganisms can be modified to make them more useful such as by inserting new metabolic pathways with the aim of producing novel metabolites or improving both new and existing processes such as the production of antibiotics and industrial enzymes. Other useful traits include herbicide resistance, antibiotic resistance, disease resistance, resistance to adverse environmental conditions (e.g., temperature, pH, salt, drought), and the like.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 51 (amino) terminus and a translation stop codon at the 31 (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

An "expression cassettes" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14 (6): 6745-6763 (1986). An exemplary implementation of this algorithm to determine percent identity of a sequence is provided by the Genetics Computer Group (Madison, WI) in the "BestFit" utility application. The default parameters for this method are described in the Wisconsin Sequence Analysis Package Program Manual, Version 8 (1995) (available from Genetics-Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=nonredundant, GenBank+EMBL+DDBJ+PDB+GenBank CDS translations+Swiss protein+Spupdate+PIR. Details of these programs can be found on the world wide web at the following internet address: ncbi.nlm.nih.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.)

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above. In the present invention, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

1.0.0 The Invention

The invention disclosed herein comprises a method of specifically modifying a genome. In one embodiment of the method, a cell having a target recombination sequence (designated attT) is transformed with a nucleic acid construct (a "targeting construct") comprising a second recombination sequence (designated attD) and one or more polynucleotides of interest. Into the same cell a recombinase is introduced that specifically recognizes the recombination sequences under conditions such that the nucleic acid sequence of interest is inserted into the genome via a recombination event between attT and attD. Alternatively, the recombinase can be introduced into the cell prior to or concurrent with introduction of the targeting construct transformation with the nucleic acid construct.

The method of the invention is based, in part, on the discovery that there exist in various genomes specific nucleic acid sequences, herein called pseudo-recombination sequences, that may be distinct from wild-type recombination sequences and that can be recognized by a site-specific recombinase and used to promote the insertion of heterologous genes or polynucleotides into the genome. The inventors have identified such pseudo-recombination sequences in a variety of organisms, including mammals and plants.

1.1.0 Recombinases

Two major families of site-specific recombinases from bacteria and unicellular yeasts have been described: the integrase family includes Cre, Flp, R, and λ integrase (Argos, et al., EMBO J. 5:433-440, 1986) and the resolvase/invertase family includes some phage integrases, such as, those of phages φC31, R4, and TP-901 (Hallet and Sherratt, FEMS Microbiol. Rev. 21:157-178, 1997). While not wishing to be bound by descriptions of mechanisms, strand exchange catalyzed by site specific recombinases typically occurs in two steps of (1) cleavage and (2) rejoining involving a covalent protein-DNA intermediate formed between the recombinase enzyme and the DNA strand(s).

The nature of the catalytic amino acid residue of the recombinase enzyme and the line of entry of the nucleophile can be different for the two recombinase families. For cleavage catalyzed by the invertase/resolvase family, for example, the nucleophile hydroxyl is derived from a serine and the leaving group is the 3'-OH of the deoxyribose. For the integrase family, the catalytic residue is, for example, a tyrosine and the leaving group is the 5'-OH. In both recombinase families, the rejoining step is the reverse of the cleavage step. Recombinases particularly useful in the practice of the invention are those that function in a wide variety of cell types, in part because they do not require any host specific factors. Suitable recombinases include Cre, Flp, R, and the integrases of phages φC31, TP901-1, R4, and the like. Some characteristics of the two recombinase families are discussed below.

1.1.1 Cre-like Recombinases

The recombinase activity of Cre has been studied as a model system for the integrases. Cre is a 38 kD protein isolated from bacteriophage P1. It catalyzes recombination at a 34 basepair stretch of DNA called loxP. The loxP site has the sequence 5'-ATAACTTCGTATA GCATACAT TATAC-GAAGTTAT-3' (SEQ ID NO: 1) consisting of two thirteen basepair palindromic repeats flanking an eight basepair core sequence. The repeat sequences act as Cre binding sites with the crossover point occurring in the core. Each repeat appears to bind one protein molecule wherein the DNA substrate (one strand) is cleaved and a protein DNA intermediate is formed having a 3'-phosphotyrosine linkage between Cre and the cleaved DNA strand. Crystallography and other studies suggest that four proteins and two loxP sites form a synapsed structure in which the DNA resembles models of four-way Holliday-junction intermediates, followed by the exchange of a second set of strands to resolve the intermediate into recombinant products (see Guo, et al, Nature 389: 40-46, 1997). The asymmetry of the core region is responsible for directionality of the recombination reaction. If the two recombination sites are repeated in the same orientation, the outcome of strand exchange is integration or excision. If the two sites are placed in the opposite orientation, the outcome is inversion of the sequence between the two sites (Yang and Mizuuchi, Structure 5: 1401-1406, 1997).

Cre has been shown to be active in a wide variety of cellular backgrounds including yeast (Sauer, Mol. Cell. Biol. 7:2087-2096, 1987), plants (Albert, et al, Plant J. 7:649-659, 1995; Dale and Ow, Gene 91:79-8S, 1990; Odell, et al, Mol. Gen. Genet. 223:369-378, 1990) and mammals, including both rodent and human cells (van Deursen, et al, Proc. Natl. Acad. Sci. USA 92:7376-7380, 1995; Agah, et al, J. Clin. Invest. 100:169-179, 1997; Baubonis, and Sauer, 21:2025-2029, 1993; Sauer and Henderson, New Biologist 2:441-449, 1990). As the loxP site is known only to occur in the P1 phage genome, use of the enzyme in other cell types requires the prior insertion of a loxP site into the genome, which using currently available technologies is generally a low-frequency and random event with all of the drawbacks inherent in such a procedure. The loxP site can be targeted to a specific location by using homologous recombination, but, again, that process occurs at a very low frequency.

Several studies have suggested the possibility that an exact match of the loxP sequence is not required for Cre-mediated recombination (Sternberg, et al, J. Mol. Biol. 150:487-507, 1981; Sauer, J. Mol. Biol. 223:911-928, 1992; Sauer, Nucleic Acids Research 24:4608-4613, 1996). The efficiency of recombination, however, has generally been three to four orders of magnitude less efficient than wild-type loxP. Sauer attempted to identify sequences similar to loxP in the human genome without success (Sauer, Nucleic Acids Research 24:4608-4613, 1996).

Flp, a recombinase of the integrase family with similar properties to Cre has been identified in strains of *Saccharomyces cerevisiae* that contain 2μ-circle DNA. Flp recognizes a DNA sequence consisting of two thirteen basepair inverted repeats flanking an eight basepair core sequence (5'-GAAGTTCCTATAC TTCTAGAA GAATAGGAACTTC -3' (SEQ ID NO: 2)) called FRT. A third repeat follows at the 3' end in the natural sequence but does not appear to be required for recombinase activity. Like Cre, Flp is functional in a wide variety of systems including bacteria (Huang, et al, J Bacteriology 179: 6076-6083, 1997), insects (Golic and Lindquist, Cell 59: 499-509, 1989; Golic and Golic, Genetics 144: 1693-1711, 1996), plants (Lyznik, et al, Nucleic Acids Res 21: 969-975, 1993) and mammals. These studies have likewise required that a FRT sequence be inserted into the genome to be modified.

A related recombinase, known as R, is encoded by the pSRi plasmid of the yeast *Zygosaccharomyces rouxii* (Araki, et al., J. Mol. Biol. 182:191-203, 1985, herein incorporated by reference). This recombinase may have properties similar to those described above.

In the context of the present invention, when a recombinase normally facilitates recombination between two recombination sites and the sites are essentially the same (e.g., loxP and Cre), the sites are designated recombinase-mediated-recombination sites (RMRS).

1.1.2 Resolvase/Integrase Recombinases

Unlike the Cre/λ integrase family of recombinases, members of the resolvase subfamily of recombinase enzymes typically contain an N-terminal catalytic domain having a high degree (>35%) of sequence homology among the subfamily members (Crellin and Rood, J Bacteriology 179(16):5148-5156, 1997; Christiansen, et al, J. Bacteriology 178(17): 5164-5S173, 1996). Like some of the Cre-type recombinases, however, some resolvases do not require host specific accessory factors (Thorpe and Smith, PNAS USA 95:5505-5510, 1998).

The process of strand exchange used by the resolvases is somewhat different than the process used by Cre. This process is described but is not intended to be limiting. The resolvases usually make cuts close to the center of the crossover site, and the top and bottom strand cuts are often staggered by 2 basepairs, leaving recessed 51 ends. A protein-DNA linkage is formed between phosphodiester from the 5' DNA end and a conserved serine residue close to the amino terminus of the recombinase. As with the Cre-like invertases, two protein units are bound at each crossover site, however, no equivalent to the Holiday junction intermediate is formed (see Stark, et al, Trends in Genetics 8(12):432-439, 1992, incorporated by reference herein).

The nucleic acid sequences recognized as recombination sites by a subset of the resolvase family, including some phage integrases, differ in several ways from the recombination site recognized by Cre. The sites used for recognition and recombination of the phage and bacterial DNAs (the native host system) are generally non-identical, although they typically have a common core region of nucleic acids. The bacterial sequence is generally called the attB sequence (bacterial attachment) and the phage sequence is called the attP sequence (phage attachment). Because they are different sequences, recombination will result in a stretch of nucleic acids (called attL or attR for left and right) that is neither an attB sequence or an attP sequence, and is probably functionally unrecognizable as a recombination site to the relevant enzyme, thus removing the possibility that the enzyme will catalyze a second recombination reaction that would reverse the first.

The individual resolvases and the nucleic acid sequences that they recognize have been less well characterized than Cre and Flp, although many of the core sequences have been identified. The core sequences of some of the resolvases useful in the practice of the invention can include, without limitation, the following sequences: φC31-5'-TTG; TP901-1-5'-TCAAT; and R4- 5'-GAAGCAGTGGTA (SEQ ID NO: 3). (See Rausch and Lehmann, NAR 19:5187-5189, 1991; Shirai, et al, J Bacteriology 173(13) :4237-4239, 1991; Crellin and Rood, J Bacteriology 179:5148-5156, 1997; Christiansen, et al, J. Bacteriology 176:1069-1076, 1994; Brondsted and Hammer, Applied & Environmental Microbiology 65:752-758, 1999; all of which are incorporated by reference herein.

Several authors have suggested that integrase or resolvase (for example, φC31 integrase) can be used to modify bacterial genomes, such as, those of *B. coli* and actinomycetes (Mascarenhas and Olson, U.S. Pat. No. 5,470,727; Cox, et al, U.S. Pat. No. 5,190,871). However, there has been no suggestion that these enzymes would be useful in the modification of non-bacterial genomes.

1.1.3 Recombination Sites

The inventors have discovered native recombination sites existing in the genomes of a variety of organisms, where the native recombination site does not necessarily have a nucleotide sequence identical to the wild-type recombination sequences (for a given recombinase); but such native recombination sites are nonetheless sufficient to promote recombination mediated by the recombinase. Such recombination site sequences are referred to herein as "pseudo-recombination sequences." For a given recombinase, a pseudo-recombination sequence is functionally equivalent to a wild-type recombination sequence, occurs in an organism other than that in which the recombinase is found in nature, and may have sequence variation relative to the wild type recombination sequences.

In the practice of the present invention, wild-type recombination sites, pseudo-recombination sites, and hybrid-recombination sites can be used in a variety of ways in the construction of targeting vectors.

Following here are non-limiting examples of how these sites may be employed in the practice of the present invention.

Identification of pseudo-recombination sequences can be accomplished, for example, by using sequence alignment and analysis, where the query sequence is the recombination site of interest (for example, a recombinase-mediated-recombination site (RMRS; e.g., loxP), or either attB and/or attP of a phage/bacterial system). Following here are some examples: if a genomic recombination site (generally designated attT) is identified using attB, then that attT site is said to be a pseudoattB site; if a genomic recombination site is identified using attP, then that attT site is said to be a pseudo-attP site; and, if a genomic recombination site is identified using an RMRS (e.g., loxP), then that attT site is said to be a pseudo-RMRS site (e.g., pseudo-loxP).

In one aspect of the present invention, the recombinase (for example, Cre) recognizes a recombination site having the following structure: flanking sequence palindrome—core sequence—flanking sequence palindrome. Such recombination sites typically comprise two approximately 10-20 base pair stretches having some palindromic character which flank an approximately 3-15 base pair core sequence.

In this aspect of the present invention, the genome of a target cell is searched for sequences having sequence identity to the selected recombination site for a given recombinase, for example, loxP (Example 1; FIG. 8). The cellular target recombination site (attT: in this example, a pseudo-loxP site) accordingly has a defined sequence. To practice the genome modification method of the present invention, a recombination sequence is placed in the targeting vector. This recombination sequence, attD, can take many forms but must be capable of participating in site specific recombination with the genomic site (attT) where the recombination is mediated by the appropriate recombinase. In this regard, non-limiting examples of attD sites include, but are not limited to, the following: attD core sequence matches the pseudo-recombination site core sequence, flanking sequences in the targeting construct are wild-type recombination sequences (this construct represents a hybrid-recombination site); or, attD core sequence matches the pseudo-recombination site core sequence, flanking sequences in the targeting construct match the pseudo-recombination site flanking sequences. Further, the core sequences between attT and attD are generally essentially the same and the flanking sequences for attD may be combinations of flanking sequences from wild-type and pseudo-recombination site sources.

The recombinase-mediated-recombination site (RMRS) of this type of recombinase, for example, Cre and Cre-like recombinases, can have the following structure: a first DNA sequence (RMRS5'), a core region A, and a second DNA sequence (RMRS3') in the relative order RMRS5'-core region A-RMRS3'. Such recombination sites typically comprise two approximately 10-20 base pair regions having palindromic characteristics (e.g., RMRS5' and RMRS3') which flank an approximately 3-15 basepair core sequence (for example, core region A). In one embodiment, e.g., when employing Cre, hybrid-recombination sites may be used where the palindromic sequences are derived from a wild-type recombination site and the core sequence is derived from a pseudo-recombination site.

Without being bound to any particular theory or mechanism of action, when such a nucleic acid construct is provided to a cell along with a site-specific recombinase, it is possible that the recombinase recognizes and binds to the flanking sequences of both hybrid-recombination sequence and the pseudo-recombination sequence from which the basepair core sequence was derived, and catalyzes the recombination between the two.

In one embodiment the attD (in the targeting construct) is a hybrid-lox sequence comprising two wild-type thirteen basepair loxP palindromes flanking a heterologous core sequence, where the core sequence corresponds to the core sequence of the pseudo-recombination sequence of attT (in the cell target). In a second embodiment the attD (in the targeting construct) is a hybrid-FRT sequence comprising two or three wild-type thirteen basepair palindromes flanking a heterologous core sequence, where the core sequences correspond to the core sequence of the pseudo-recombination sequence of attT (in the cell target).

Example 2 describes methods for testing whether a putative recombination site is functional as a pseudo-recombination site for recombination mediated by the selected site specific recombinase and also methods for assessing the efficiency of recombination.

In a second aspect of the present invention, the recombinase (for example, φC31) recognizes a recombination site where sequence of the 5' region of the recombination site can differ from the sequence of the 3' region of the recombination sequence. For example, for the phage φC31 attP (the phage attachment site), the core region is 5'-TTG-3' the flanking sequences on either side are represented here as attP5' and attP3', the structure of the attP recombination site is, accordingly, attP5'-TTG-attP3'. Correspondingly, for the native bacterial genomic target site (attB) the core region is 5'-TTG-3', and the flanking sequences on either side are represented here as attB5' and attB3', the structure of the attB recombination site is, accordingly, attB5'-TTG-attB3'. After a single-site, φC31 integrase mediated, recombination event takes place the result is the following recombination product: attB5'-TTG-attP3' {φC31 vector sequences}attP5'-TTG-attB3'. Typically, after recombination the post-recombination recombination sites are no longer able to act as substrate for the φC31 recombinase. This results in stable integration with little or no recombinase mediated excision. These structures are represented in a more generic way as follows: circular targeting vector comprising the recombination site (attD) and a polynucleotide of interest—attD5'-core-attD3'; pseudo-recombination site (attT)—attT5'-core-attT3'; post recombination structure—attT5'-recombination product site (e.g., core)-attD3' {polynucleotide sequences of interest}attD5'-recombination product site (e.g., core)-attT3'. The recombination product site sequence can comprise a core identical to the original core sequence. However, the complete post-recombination, recombination sites (for example, attT5'-recombination product site (e.g., core)-attD3') generally no longer provide a usable substrate for the recombinase.

In this aspect, when selecting pseudo-recombination sites in a target cell (attT), the genomic sequences of the target cell can be searched for suitable pseudo-recombination sites using either the attP or attB sequences associated with a particular recombinase. Functional sizes and the amount of heterogeneity that can be tolerated in these recombination sequences can be evaluated, for example, as described in Examples 8 and 9.

When a pseudo-recombination site is identified using either attP or attB search sequences, the other recombination site can be used in the targeting construct. For example, if attP for a selected recombinase is used to identify a pseudo-recombination site in the target cell genome, then the wild-type attB sequence can be used in the targeting construct. In an alternative example, if attB for a selected recombinase is used to identify a pseudo-recombination site in the target cell genome, then the wild-type attP sequence can be used in the targeting construct.

The targeting constructs contemplated by the invention may contain additional nucleic acid fragments such as control sequences, marker sequences, selection sequences and the like as discussed below.

1.2.0 Targeting Constructs and Methods of the Present Invention

The present invention also provides means for targeted insertion of a polynucleotide (or nucleic acid sequence(s)) of interest into a genome by, for example, (i) providing a recombinase, wherein the recombinase is capable of facilitating recombination between a first recombination site and a second recombination site, (ii) providing a targeting construct having a first recombination sequence and a polynucleotide of interest, (iii) introducing the recombinase and the targeting construct into a cell which contains in its nucleic acid the second recombination site, wherein said introducing is done under conditions that allow the recombinase to facilitate a recombination event between the first and second recombination sites.

Historically, the attachment site in a bacterial genome is designated "attB" and in a corresponding bacteriophage the site is designated "attP". A recombination site in a cell of interest is designated herein as "attT". A recombination site in a targeting vector is referred to herein as "attD".

In one aspect of the present invention, at least one pseudo-recombination site for a selected recombinase is identified in a target cell of interest (attT). These sites can be identified by several methods including searching all known sequences derived from the cell of interest against a wild-type recombination site (e.g., attB or attP) for a selected recombinase (e.g., as described in Example 1). The functionality of pseudo-recombination sites identified in this way can then be empirically evaluated following the teachings of the present specification to determine their ability to participate in a recombinase-mediated recombination event.

1.2.1 Targeting Constructs of the Present Invention

A targeting construct, to direct integration to this pseudo-recombination site, would then comprise a recombination site (attD) wherein the recombinase can facilitate a recombination event between attT and attD, and a polynucleotide of interest. Polynucleotides of interest can include, but are not limited to, expression cassettes encoding polypeptide products. The targeting constructs are typically circular and may also contain selectable markers, an origin of replication, and other elements. Targeting constructs of the present invention are typically circular.

A variety of expression vectors are suitable for use in the practice of the present invention, both for prokaryotic expression and eukaryotic expression. In general, the targeting construct will have one or more of the following features: a promoter, promoter-enhancer sequences, a selection marker sequence, an origin of replication, an inducible element sequence, an epitope—tag sequence, and the like.

Promoter and promoter-enhancer sequences are DNA sequences to which RNA polymerase binds and initiates transcription. The promoter determines the polarity of the transcript by specifying which strand will be transcribed. Bacterial promoters consist of consensus sequences, -35 and -10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g. AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable (i.e., inducible or derepressible). Inducible elements are DNA sequence elements which act in conjunction with promoters and bind either repressors (e.g. lacO/LAC Iq repressor system in $E.\ coli$) or inducers (e.g. gal1/GAL4 inducer system in yeast). In either case, transcription is virtually "shut off", until the promoter is derepressed or induced, at which point transcription is "turned-on."

Examples of constitutive promoters include the int promoter of bacteriophage $\lambda$, the bla promoter of the $\beta$-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, AraC and gal promoters of $E.\ coli$, the $\alpha$-amylase (Ulmanen Ett at., J. Bacteriol. 162:176-182, 1985) and the sigma-28-specific promoters of $B.\ subtilis$ (Gilman et al., Gene sequence 32:11-20 (1984)), the promoters of the bacteriophages of $Bacillus$ (Gryczan, In: The Molecular Biology of the Bacilli, Academic Press, Inc., NY (1982)), $Streptomyces$ promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Preferred eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoters), tetracycline-responsive promoter, and the like.

Exemplary promoters for use in the present invention are selected such that they are functional in cell type (and/or animal or plant) into which they are being introduced.

Selection markers are valuable elements in expression vectors as they provide a means to select for growth of only those cells that contain a vector. Such markers are of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media that lacks that essential component.

Common selectable marker genes include those for resistance to antibiotics such as ampicillin, tetracycline, kanamycin, bleomycin, streptomycin, hygromycin, neomycin, Zeocin™, and the like. Selectable auxotrophic genes include, for example, hisD, that allows growth in histidine free media in the presence of histidinol.

A further element useful in an expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in expression vectors employed herein include $E.\ coli$ oriC, colE1 plasmid origin, 2$\mu$ and ARS (both useful in yeast systems), sf1, SV40, EBV oriP (useful in mammalian systems), and the like.

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr, chitin binding domain, and the like.

A further useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The foregoing elements can be combined to produce expression vectors suitable for use in the methods of the invention. Those of skill in the art would be able to select and combine the elements suitable for use in their particular system in view of the teachings of the present specification. Suitable prokaryotic vectors include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)). *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include pli101 (Kendall et al., J. Bacteriol. 169:4177-4183, 1987), and *streptomyces* bacteriophages such as ϕC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suitable eukaryotic plasmids include, for example, BPV, EBV, vaccinia, SV40, 2-micron circle, pcDNA3.1, pcDNA3.1/GS, pYES2/GS, pMT, p IND, pIND(Sp1), pVgRXR (Invitrogen), and the like, or their derivatives. Such plasmids are well known in the art (Botstein et al., Miami Wntr. SyTnp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et al., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

The targeting cassettes described herein can be constructed utilizing methodologies known in the art of molecular biology (see, for example, Ausubel or Maniatis) in view of the teachings of the specification. As described above, the targeting constructs are assembled by inserting, into a suitable vector backbone, an attD (recombination site), polynucleotides encoding sequences of interest operably linked to a promoter of interest; and, optionally a sequence encoding a positive selection marker.

A preferred method of obtaining polynucleotides, including suitable regulatory sequences (e.g., promoters) is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. After amplification, the resulting fragments can be detected by agarose gel electrophoresis followed by visualization with ethidium bromide staining and ultraviolet illumination.

The expression cassettes, targeting constructs, vectors, recombinases and recombinase-coding sequences of the present invention can be formulated into kits.

Components of such kits can include, but are not limited to, containers, instructions, solutions, buffers, disposables, and hardware.

1.2.2 Introducing Recombinases

In the methods of the invention a site-specific recombinase is introduced into a cell whose genome is to be modified. Methods of introducing functional proteins into cells are well known in the art. Introduction of purified recombinase protein ensures a transient presence of the protein and its function, which is often a preferred embodiment. Alternatively, a gene encoding the recombinase can be included in an expression vector used to transform the cell. It is generally preferred that the recombinase be present for only such time as is necessary for insertion of the nucleic acid fragments into the genome being modified. Thus, the lack of permanence associated with most expression vectors is not expected to be detrimental.

The recombinases used in the practice of the present invention can be introduced into a target cell before, concurrently with, or after the introduction of a targeting vector. The recombinase can be directly introduced into a cell as a protein, for example, using liposomes, coated particles, or microinjection. Alternately, a polynucleotide encoding the recombinase can be introduced into the cell using a suitable expression vector. The targeting vector components described above are useful in the construction of expression cassettes containing sequences encoding a recombinase of interest. Expression of the recombinase is typically desired to be transient. Accordingly, vectors providing transient expression of the recombinase are preferred in the practice of the present invention. However, expression of the recombinase can be regulated in other ways, for example, by placing the expression of the recombinase under the control of a regulatable promoter (i.e., a promoter whose expression can be selectively induced or repressed).

Sequences encoding recombinases useful in the practice of the present invention are known and include, but are not limited to, the following: Cre—Sternberg, et al., J. Mol. Biol. 187:197-212; ϕC31—Kuhstoss and Rao, J. Mol. Biol. 222: 897-908, 1991; TP901-1—Christiansen, et al., J. Bact. 178: 5164-5173, 1996; R4—Matsuura, et al., J. Bact. 178:3374-3376, 1996.

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

1.2.3 Cells

Cells suitable for modification employing the methods of the invention include both prokaryotic cells and eukaryotic cells, provided that the cell's genome contains a pseudo-recombination sequence. Prokaryotic cells are cells that lack a defined nucleus. Examples of suitable prokaryotic cells include bacterial cells, mycoplasmal cells and archaebacterial cells. Particularly preferred prokaryotic cells include those that are useful either in various types of test systems (discussed in greater detail below) or those that have some industrial utility such as *Klebsiella oxytoca* (ethanol production), *Clostridium acetobutylicum* (butanol production), and the like (see Green and Bennet, Biotech & Bioengineering 58:215-221, 1998; Ingram, et al, Biotech & Bioengineering 58:204-206, 1998). Suitable eukaryotic cells include both animal cells (such as from insect, rodent, cow, goat, rabbit, sheep, non-human primate, human, and the like) and plant cells (such as rice, corn, cotton, tobacco, tomato, potato, and the like). Cell types applicable to particular purposes are discussed in greater detail below.

Yet another embodiment of the invention comprises isolated genetically engineered cells. Suitable cells may be prokaryotic or eukaryotic, as discussed above. The genetically engineered cells of the invention may be unicellular organisms or may be derived from multicellular organisms. By "isolated" in reference to genetically engineered cells derived from multicellular organisms it is meant the cells are outside a living body, whether plant or animal, and in an artificial environment. The use of the term isolated does not imply that the genetically engineered cells are the only cells present.

In one embodiment, the genetically engineered cells of the invention contain any one of the nucleic acid constructs of the invention. In a second embodiment, a recombinase that specifically recognizes recombination sequences is introduced into genetically engineered cells containing one of the nucleic acid constructs of the invention under conditions such that the nucleic acid sequence(s) of interest will be inserted into the genome. Thus, the genetically engineered cells possess a modified genome. Methods of introducing such a recombinase are well known in the art and are discussed above.

The genetically engineered cells of the invention can be employed in a variety of ways. Unicellular organisms can be modified to produce commercially valuable substances such as recombinant proteins, industrial solvents, industrially useful enzymes, and the like. Preferred unicellular organisms include fungi such as yeast (for example, *S. pombe, Pichia pastoris, S. cerevisiae* (such as INVSc1), and the like) *Aspergillis*, and the like, and bacteria such as *Klebsiella, Streptomyces*, and the like.

Isolated cells from multicellular organisms can be similarly useful, including insect cells, mammalian cells and plant cells. Mammalian cells that may be useful include those derived from rodents, primates and the like. They include HeLa cells, cells of fibroblast origin such as VERO, 3T3 or CHOK1, HEK 293 cells or cells of lymphoid origin (such as 32D cells) and their derivatives. Preferred mammalian host cells include nonadherent cells such as CHO, 32D, and the like.

In addition, plant cells are also available as hosts, and control sequences compatible with plant cells are available, such as the cauliflower mosaic virus 35S and 19S, nopaline synthase promoter and polyadenylation signal sequences, and the like. Appropriate transgenic plant cells can be used to produce transgenic plants.

Another preferred host is an insect cell, for example from the *Drosophila* larvae. Using insect cells as hosts, the *Drosophila* alcohol dehydrogenase promoter can be used (Rubin, Science 240:1453-1459, 1988). Alternatively, baculovirus vectors can be engineered to express large amounts of peptide encoded by a desired nucleic acid sequence in insect cells (Jasny, Science 238:1653, 1987); Miller et al., In: Genetic Engineering (1986), Setlow, J. K., et al., eds., Plenum, Vol. 8, pp. 277-297).

The genetically engineered cells of the invention are additionally useful as tools to screen for substances capable of modulating the activity of a protein encoded by a nucleic acid fragment of interest. Thus, an additional embodiment of the invention comprises methods of screening comprising contacting genetically engineered cells of the invention with a test substance and monitoring the cells for a change in cell phenotype, cell proliferation, cell differentiation, enzymatic activity of the protein or the interaction between the protein and a natural binding partner of the protein when compared to test cells not contacted with the test substance.

A variety of test substances can be evaluated using the genetically engineered cells of the invention including peptides, proteins, antibodies, low molecular weight organic compounds, natural products derived from, for example, fungal or plant cells, and the like. By "low molecular weight organic compound" it is, meant a chemical species with a molecular weight of generally less than 500-1000. Sources of test substances are well known to those of skill in the art.

Various assay methods employing cells are also well known by those skilled in the art. They include, for example, assays for enzymatic activity (Hirth, et al, U.S. Pat. No. 5,763, 198, issued Jun. 9, 1998), assays for binding of a test substance to a protein expressed by the genetically engineered cells, assays for transcriptional activation of a reporter gene, and the like.

Cells modified by the methods of the present invention can be maintained under conditions that, for example, (i) keep them alive but do not promote growth, (ii) promote growth of the cells, and/or (iii) cause the cells to differentiate or dedifferentiate. Cell culture conditions are typically permissive for the action of the recombinase in the cells, although regulation of the activity of the recombinase may also be modulated by culture conditions (e.g., raising or lowering the temperature at which the cells are cultured). For a given cell, cell-type, tissue, or organism, culture conditions are known in the art.

2.0.0 Transgenic Plants and Non-Human Animals

In another embodiment, the present invention comprises transgenic plants and nonhuman transgenic animals whose genomes have been modified by employing the methods and compositions of the invention. Transgenic animals may be produced employing the methods of the present invention to serve as a model system for the study of various disorders and for screening of drugs that modulate such disorders.

A "transgenic" plant or animal refers to a genetically engineered plant or animal, or offspring of genetically engineered plants or animals. A transgenic plant or animal usually contains material from at least one unrelated organism, such as, from a virus. The term "animal" as used in the context of transgenic organisms means all species except human. It also includes an individual animal in all stages of development, including embryonic and fetal stages. Farm animals (e.g., chickens, pigs, goats, sheep, cows, horses, rabbits and the like), rodents (such as mice), and domestic pets (e.g., cats and dogs) are included within the scope of the present invention. In a preferred embodiment, the animal is a mouse or a rat.

The term "chimeric" plant or animal is used to refer to plants or animals in which the heterologous gene is found, or in which the heterologous gene is expressed in some but not all cells of the plant or animal.

The term transgenic animal also includes a germ cell line transgenic animal A "germ cell line transgenic animal" is a transgenic animal in which the genetic information provided by the invention method has been taken up and incorporated into a germ line cell, therefore conferring the ability to transfer the information to offspring. If such offspring, in fact, possess some or all of that information, then they, too, are transgenic animals.

Methods of generating transgenic plants and animals are known in the art and can be used in combination with the teachings of the present application.

In one embodiment, a transgenic animal of the present invention is produced by introducing into a single cell embryo a nucleic acid construct, comprising an attD recombination site capable of recombining with an attT recombination site found within the genome of the organism from which the cell was derived and a nucleic acid fragment of interest, in a manner such that the nucleic acid fragment of interest is stably integrated into the DNA of germ line cells of the mature animal and is inherited in normal Mendelian fashion. In this embodiment, the nucleic acid fragment of interest can be any one of the fragment described previously. Alternatively, the nucleic acid sequence of interest can encode an exogenous product that disrupts or interferes with expression of an endogenously produced protein of interest, yielding a transgenic animals with decreased expression of the protein of interest.

A variety of methods are available for the production of transgenic animals. A nucleic acid construct of the invention can be injected into the pronucleus, or cytoplasm, of a fertilized egg before fusion of the male and female pronuclei, or injected into the nucleus of an embryonic cell (e.g., the nucleus of a two-cell embryo) following the initiation of cell division (Brinster, et al., Proc. Nat. Acad. Sci. USA 82: 4438, 1985). Embryos can be infected with viruses, especially retroviruses, modified with an attD recombination site and a nucleic acid sequence of interest. The cell can further be treated with a site-specific recombinase as described above to promote integration of the nucleic acid sequence of interest into the genome.

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099-1112, 1990). Rodents suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47:897-905, 1991). Other procedures for introduction of DNA into tissues of animals are described in U.S. Pat. No. 4,945,050 (Sandford et al., Jul. 30, 1990).

Totipotent or pluripotent stem cells derived from the inner cell mass of the embryo and stabilized in culture can be manipulated in culture to incorporate nucleic acid sequences employing invention methods. A transgenic animal can be produced from such cells through injection into a blastocyst that is then implanted into a foster mother and allowed to come to term.

Methods for the culturing of stem cells and the subsequent production of transgenic animals by the introduction of DNA into stem cells using methods such as electroporation, calcium phosphate/DNA precipitation, microinjection, liposome fusion, retroviral infection, and the like are also are well known to those of ordinary skill in the art. See, for example, Teratocarcinomas and Embryonic Stem Cells, A Practical Approach, E. J. Robertson, ed., IRL Press, 1987). Reviews of standard laboratory procedures for microinjection of heterologous DNAs into mammalian (mouse, pig, rabbit, sheep, goat, cow) fertilized ova include: Hogan et al., *Manipulating the Mouse Embryo* (Cold Spring Harbor Press 1986); Krimpenfort et al., 1991, *Bio/Technology* 9:86; Palmiter et al., 1985, Cell 41:343; Kraemer et al., *Genetic Manipulation of the Early Mammalian Embryo* (Cold Spring Harbor Laboratory Press 1985); Hammer et al., 1985, Nature, 315:680; Purcel et al., 1986, *Science,* 244:1281; Wagner et al., U.S. Pat. No. 5,175,385; Krimpenfort et al., U.S. Pat. No. 5,175,384, the respective contents of which are incorporated by reference.

The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others (see Houdebine and Chourrout, supra; Pursel, et al., Science 244:1281-1288, 1989; and Simms, et al., Bio/Technology 6:179-183, 1988). Animals carrying the transgene can be identified by methods well known in the art, e.g., by dot blotting or Southern blotting.

The term transgenic as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with loss of function that has been achieved by use of the invention vector. In one embodiment, transgenic animals having gene knockouts are those in which the target gene has been rendered nonfunctional by an insertion targeted to the gene to be rendered non-functional by targeting a pseudo-recombination site located within the gene sequence.

3.0.0 Gene Therapy and Disorders

A further embodiment of the invention comprises a method of treating a disorder in a subject in need of such treatment. In one embodiment of the method, at least one cell or cell type (or tissue, etc.) of the subject has a target recombination sequence (designated attT). This cell(s) is transformed with a nucleic acid construct (a "targeting construct") comprising a second recombination sequence (designated attD) and one or more polynucleotides of interest (typically a therapeutic gene). Into the same cell a recombinase is introduced that specifically recognizes the recombination sequences under conditions such that the nucleic acid sequence of interest is inserted into the genome via a recombination event between attT and attD. Subjects treatable using the methods of the invention include both humans and non-human animals. Such methods utilize the targeting constructs and recombinases of the present invention.

A variety of disorders may be treated by employing the method of the invention including monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like.

Infectious diseases treatable by employing the methods of the invention include infection with various types of virus including human T-cell lymphotropic virus, influenza virus, papilloma virus, hepatitis virus, herpes virus, Epstein-Bar virus, immunodeficiency viruses (HIV, and the like), cytomegalovirus, and the like. Also included are infections with other pathogenic organisms such as *Mycobacterium Tuberculosis*, *Mycoplasma pneumoniae*, and the like or parasites such as *Plasmadium falciparum*, and the like.

The term "acquired disorder" as used herein refers to a noncongenital disorder. Such disorders are generally considered more complex than monogenic disorders and may result from inappropriate or unwanted activity of one or more genes. Examples of such disorders include peripheral artery disease, rheumatoid arthritis, coronary artery disease, and the like.

A particular group of acquired disorders treatable by employing the methods of the invention include various cancers, including both solid tumors and hematopoietic cancers such as leukemias and lymphomas. Solid tumors that are treatable utilizing the invention method include carcinomas, sarcomas, osteomas, fibrosarcomas, chondrosarcomas, and the like. Specific cancers include breast cancer, brain cancer, lung cancer (non-small cell and small cell), colon cancer, pancreatic cancer, prostate cancer, gastric cancer, bladder cancer, kidney cancer, head and neck cancer, and the like.

The suitability of the particular place in the genome is dependent in part on the particular disorder being treated. For example, if the disorder is a monogenic disorder and the desired treatment is the addition of a therapeutic nucleic acid encoding a non-mutated form of the nucleic acid thought to be the causative agent of the disorder, a suitable place may be a region of the genome that does not encode any known protein and which allows for a reasonable expression level of the added nucleic acid. Methods of identifying suitable places in the genome are well known in the art and described further in the Examples below.

The nucleic acid construct useful in this embodiment is additionally comprised of one or more nucleic acid fragments of interest. Preferred nucleic acid fragments of interest for use in this embodiment are therapeutic genes and/or control regions, as previously defined. The choice of nucleic acid sequence will depend on the nature of the disorder to be treated. For example, a nucleic acid construct intended to treat hemophilia B, which is caused by a deficiency of coagulation factor IX, may comprise a nucleic acid fragment encoding functional factor IX. A nucleic acid construct intended to treat obstructive peripheral artery disease may comprise nucleic acid fragments encoding proteins that stimulate the growth of new blood vessels, such as, for example, vascular endothelial growth factor, platelet-derived growth factor, and the like. Those of skill in the art would readily recognize which nucleic acid fragments of interest would be useful in the treatment of a particular disorder.

The nucleic acid construct can be administered to the subject being treated using a variety of methods. Administration can take place in vivo or ex viva. By "in vivo," it is meant in the living body of an animal. By "ex vivo" it is meant that cells or organs are modified outside of the body, such cells or organs are typically returned to a living body.

Methods for the therapeutic administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like. Techniques well known in the art for the transfection of cells (see discussion above) can be used for the ex vivo administration of nucleic acid constructs. The exact formulation, route of administration and dosage can be chosen by the individual physician in view of the patient's condition. (See e.g. Fingl et al., 1975, in "The Pharmacological Basis of Therapeutics", Ch. 1 p 1).

It should be noted that the attending physician would know how to and when to terminate, interrupt, or adjust administration due to toxicity, to organ dysfunction, and the like. Conversely, the attending physician would also know how to adjust treatment to higher levels if the clinical response were not adequate (precluding toxicity). The magnitude of an administered dose in the management of the disorder being treated will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

In general at least 1-10% of the cells targeted for genomic modification should be modified in the treatment of a disorder. Thus, the method and route of administration will optimally be chosen to modify at least 0.1-1% of the target cells per administration. In this way, the number of administrations can be held to a minimum in order to increase the efficiency and convenience of the treatment.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The subject being treated will additionally be administered a recombinase that specifically recognizes the attT and attD recombination sequences that are selected for use. The particular recombinase can be administered by including a nucleic acid encoding it as part of a nucleic acid construct, or as a protein to be taken up by the cells whose genome is to be modified. Methods and routes of administration will be similar to those described above for administration of a targeting construct comprising a recombination sequence and nucleic acid sequence of interest. The recombinase protein is likely to only be required for a limited period of time for integration of the nucleic acid sequence of interest. Therefore, if introduced as a recombinase gene, the vector carrying the recombinase gene will lack sequences mediating prolonged retention. For example, conventional plasmid DNA decays rapidly in most mammalian cells. The recombinase gene may also be equipped with gene expression sequences that limit its expression. For example, an inducible promoter can be used, so that recombinase expression can be temporally limited by limited exposure to the inducing agent. One such exemplary group of promoters are tetracycline-responsive promoters the expression of which can be regulated using tetracycline or doxycycline.

The invention will now be described in greater detail by reference to the following non-limiting Examples.

EXAMPLES

Example 1

Identification of Pseudo-recombination Sequences

The following example describes the identification of pseudo-loxP sequences by computer search. Similar procedures can be used to identify other pseudo-recombination sequences.

The find patterns algorithm of the Wisconsin Software Package Version 9.0 developed by the Genetics Computer Group (GCG; Madison, Wis.), was used to screen all sequences in the GenBank database (Benson et al., 1998, Nucleic Acids Res. 26, 1-7). Default parameters are given below. Patterns resembling the wild-type loxP sequence, called pseudo-loxP sites (ψlox) herein, were sought. The results from two different search strategies (Patterns 1 and #2, see below) were pooled.

The wild-type loxP site is 34 base pairs long and consists of two identical thirteen-basepair palindromes, separated by an eight-basepair core. It has been demonstrated that, while strand cutting and exchange take place in the eight-basepair core, the DNA sequence of most of this core is not critical, as long as it matches between the two sites that are to recombine (Hoess et al., 1986, Nucleic Acids Res. 14, 2287-2300; Sauer, 1996, Nucleic Acids Res. 24, 4608-4613). Therefore, most of these bases were set as n's in the search algorithm. Nucleic acid constructs created using the principles embodied in the invention allow for full control over the sequence of the incoming lox site, as its eight-basepair core can be made to match that of the genomic site being targeted. This feature of the recombination reaction gives the desired level of specificity, allowing targeting of only one ψlox site in the genome.

Previous studies have suggested that the central bases of the thirteen-basepair palindrome, those closest to the eight-basepair core, are important for Cre recognition. Therefore, greater weight was given to matching the inner four or five positions of the palindrome.

Using search Pattern #1, a search was constructed in such a way that the sequences returned by the search program would only look for resemblance in the thirteenbasepair palindromic regions of the loxP site. The sequence entered into the search algorithm is shown below:

```
                                        (SEQ ID NO: 4)
Pattern #1: ATAACTTCGTATA(n){8}TATACGAAGTTAT.
```

The (n) {8} allows the program to substitute any eight nucleotides in the region between the two thirteen-basepair inverted repeats and only look for similarity to the thirteen-basepair inverted repeats. Both strands were searched and no gaps or extensions were allowed.

When the search was conducted allowing for a maximum of eight mismatches, a large number of hits were obtained in the primate database. The total number of sequences searched was 73,825, representing 118,684,866 basepairs of sequence. The hits obtained from this search were then reviewed to identify likely pseudo-loxP candidates. Sequences having exact matches of at least four or five nucleotides immediately adjacent to the core on each side were given preference because mismatches more than five nucleotides away from the core on either side may be tolerated to some extent by Cre recombinase. A similar search was undertaken with the rodent database.

Search Pattern #2 made use of additional search criteria derived from structural studies of Cre. The crystal structure at 2.4 angstrom resolution of Cre recombinase complexed with loxP DNA reveals that contact is made between Cre and its target site at certain bases (Guo et al., 1997, Nature 389, 40-46). Footprinting with Fe-EDTA using Cre bound to the loxP site also reveals points of contact between Cre and bases in the loxP site (Hoess et al., 1990, J. Mol. Biol. 216, 873-15 882). These bases can be weighted more heavily to favor matching with the wild-type site. The search formula for determining a fit to these structural criteria was as follows for the 34-basepair lox site:

```
                                        (SEQ ID NO: 5)
Pattern #2: ATnACnnCnTATA nnnTAnnn TATRnGnnGTnAT.
```

Again, both strands were searched and no gaps or extensions were allowed. A search demanding four or fewer mismatches with the specified 16 basepairs yielded an extensive list of matches with the extant DNA sequences.

Searches were done in GenBank in the Primate, Rodent, Invertebrate, Plant, Fungus, and Bacteria databases. Some of the sites identified using these methods are shown in FIGS. 8A and 8B. The core sequences are shown in boldface type.

Example 2

In vitro Excision Assay of Pseudo-lox Sites in Bacteria and Human Cells

The following example demonstrates that the pseudo-recombination sequences of the invention are functional as sites for recombination of a nucleic acid sequence by a site-specific recombinase.

Figure 1B:
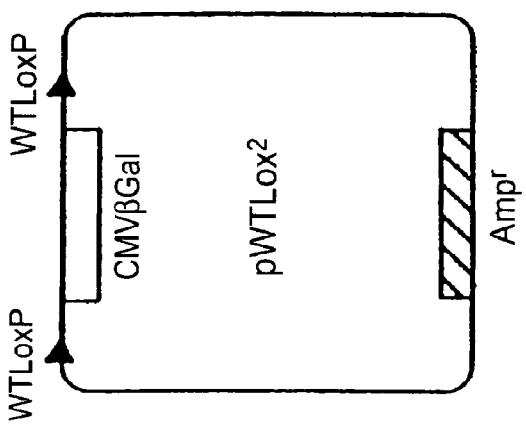
Figure 1A:
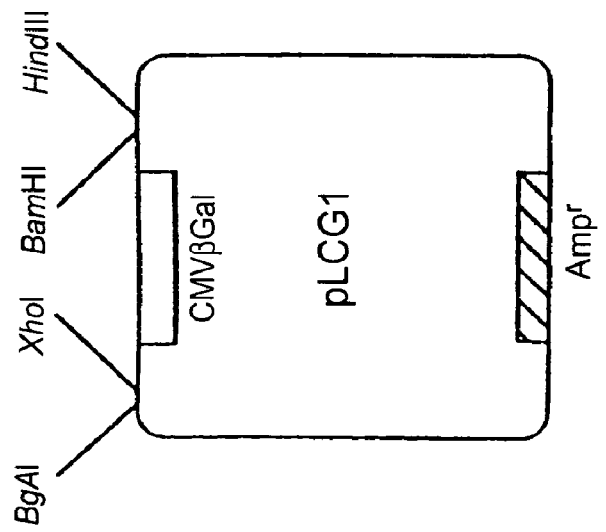

A negative control plasmid, pLCG1 (FIG. 1A), was created by inserting a 4.3-kb XbaI-BspHI fragment containing the lacz gene, encoding β-galactosidase, driven by the CMV promoter (from pCMVSPORT-βgal, Gibco/BRL) into the EcoRV site of pLitmus29 (New England Biolabs, Beverly, Mass.) in the opposite orientation to the LacZα gene already present in the plasmid. This plasmid was then used as a base for the construction of other plasmids used in the excision assay. A very similar negative control plasmid, pL2β50, was used in some of the experiments in place of pLCG1. Briefly, annealed oligonucleotides containing the lox sites being tested and a marker restriction enzyme site were directionally cloned into the BamHI-HindIII sites on one side and the BglII-XhoI sites on the other side of the CMV-lacZ construct. This cloning was carried out to ensure that Cre-induced site-specific recombination would result in excision of the lacz marker gene. A schematic representation of the plasmids is shown in FIGS. 1A through 1C. FIG. 1D shows the DNA sequences of the lox sites from pWTLox$^2$ shown in FIG. 1B (top line of FIG. 1D) and plasmid p ψloxh7q21 shown in FIG. 1C (bottom lines of FIG. 1D).

The positive control plasmid used in the excision assay (pWTLox$^2$, FIG. 1B) had the 34-bp wild-type loxP site cloned into both the BamHI-HindIII site and the BglII-XhoI site. The test plasmids had a pseudo-recombination site cloned into the BglII-XhoI site and a recombination site containing the 13-bp palindromic repeats of loxP flanking the core sequence of the pseudo-recombination sequence cloned into the BamHI-HindIII site.

The bacterial strain used for the excision assay, 294-Cre (Buchholz, et al, Nucleic Acids Research 24:3318-3319, 1996) has been designed to constitutively express Cre recombinase at 37° C.

Approximately 1 ng of the DNA being tested was electrotransformed into the 294-Cre strain of E. coli using the Bio-Rad Gene Pulser (BioRad Laboratories, CA) at a field strength of 12.5 kV/cm, with a capacitance of 25 µF and resistance of 200Ω. Aliquots of the transformation mix were spread on plates containing ampicillin (100 µg/ml), methicillin (100 µg/ml), and X-gal (60 µg/ml). The plates were incubated at 37° C. for 18 hours, after which they were scored for the presence of blue and white colonies. Bacteria containing the parent plasmid pLCG1 generated a blue bacterial colony when grown on these plates, whereas bacteria containing a plasmid from which lacZ sequence has been excised generated a white colony. The excision frequency was defined as the ratio of the number of white colonies to the total number of colonies, expressed as a percentage.

As shown in Table 1 below, the excision frequency was close to 100% when the wild-type loxP sequences were present on the plasmid (positive control) and no excision was observed when no loxP sites were present.

TABLE 1

| lox Site Tested | Mean Recombination Efficiency (%) |
| --- | --- |
| none | 0.00 |
| loxP | 98.9 |
| ψlox h7q21 | 11.5 |
| ψlox h7q31 | 8.9 |
| ψlox hXp22 | 99.0 |
| ψlox h5p15 | 1.4 |
| ψlox m9 | 4.0 |
| ψlox m5 | 98.7 |

The results above are based on from 4 to 13 separate experiments for each plasmid tested. The data indicate that pseudo-recombination sequences are functional, and some pseudo-recombination sequences (ψlox hXp22 and ψlox m5) promote recombination at very high frequencies, comparable to the wild-type loxP sequence.

In conjunction with the data of Example 1, these recombination efficiency results help identify which basepairs within loxP are most critical for Cre binding. A strict correlation between the number of mismatches and the recombination efficiency was not observed. Therefore, it is clear that matches at specific positions are more important than overall homology. These results are consistent with the idea that the four bases flanking the core are important, as the ψlox hp15 site, that has a mismatch in this region while otherwise having good matches, had the lowest recombination frequency. The wild-type core sequence was not required. For example, ψlox m5, which had a recombination frequency indistinguishable from that of loxP, had no matches to loxP in the 8-bp core. However, the best sites had only A and T basepairs in the central two positions of the core, indicating that this feature may be important.

The four ψlox sequences identified by using Pattern #2, ψlox hXp22, ψlox h5 p15, ψlox m5, and ψlox m9, included the two ψlox sites with the highest excision efficiencies, ψlox hXp22 and ψlox m5, indistinguishable from loxP. On the other hand, ψlox h5 p15, also obtained using Pattern #2, had the lowest recombination efficiency of the sites tested, probably because it contained a mismatch in the four positions nearest the core. These results suggest that while these first four positions are critical, the requirement for matching at the first five positions, used in screening the sites obtained with search Pattern #1, was overly restrictive. Good results would be obtained by using Pattern #2 in combination with a stringent requirement for matching at the first four positions from the core.

A similar assay was carried out in mammalian cells Briefly, a plasmid expressing Cre, pBS185 (Life Technologies Inc., Grand Island, N.Y.) was modified by the insertion of a kanamycin resistance gene into the unique ScaI site to create pBS185-Kan. This modification renders cells transfected with plasmid resistant to kanamycin but sensitive to ampicillin. Approximately 2 µg of plasmid pBS185-Kan and 50 ng of one of the plasmids used in the bacterial assay described above were transfected into 293 (ATCC Accession No. 1573), human embryonic kidney cells, using LipofectAmine (Life Technologies) following the manufacturer's recommendations. The transfected cells were treated with DNaseI 24 hours after transfection. The cells were grown at 37° C. in Dulbecco's Modified Eagle medium (DMEM) for 72 hours after which low molecular weight DNA was isolated from the cells by Hirt extraction (Hirt, J. Mo. Biol. 26:365-369, 1967). The plasmid DNA was electrotransformed into E. coli strain DH10B (Life Technologies) under the conditions described above. Aliquots of the transformed bacteria were grown on amp/meth/X-gal plates as described above and scored for the presence of blue and white colonies.

Figure 2:
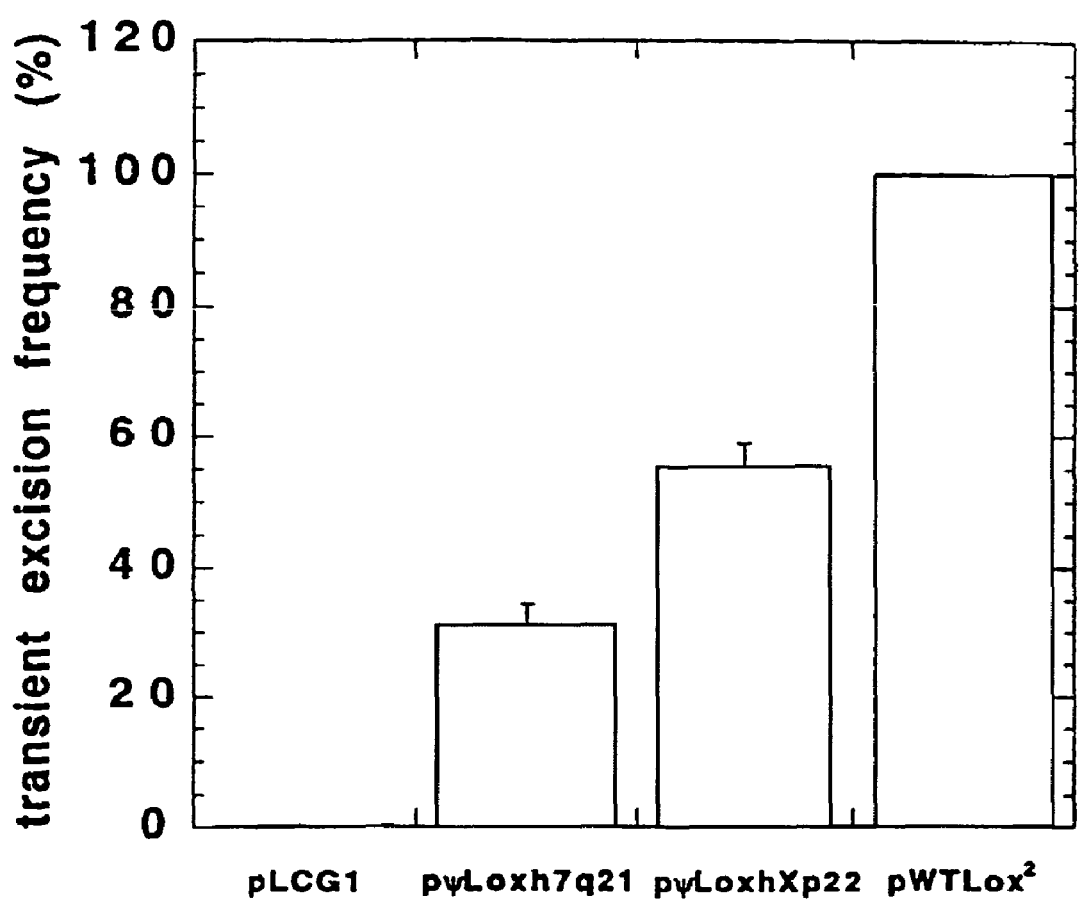
FIG. 2 shows the results of an excision assay performed in human cells as described in the examples. Each of the tested plasmids was transfected into human 293 cells along with a Cre expression plasmid. After 72 hours, DNA was transformed into E. coli and recombinants scored. The transient excision frequency is expressed as a percentage, where the value for pWTLox² is set at 100%.

Exemplary results are shown in FIG. 2. The frequency of excision seen in a mammalian cell background demonstrates the predictive nature of the bacterial assay system and demonstrates that the pseudo-recombination sequences of the invention are active substrates for recombinase-mediated recombination in a mammalian cell environment.

The ψlox h7q21 and ψlox hXp22 sites may mediate integration into the human genome. The ψlox h7q21 site is located in the q21 region of chromosome 7, while the ψlox hXp22 site is situated in band p22 of the X chromosome. The existence of these sequences in the human genome was verified by sequencing the appropriate PCR fragments covering the sites from human genomic DNA. Neither site is located in a coding sequence or a known gene.

Example 3

In vitro Transient Integration Assay of Pseudo-lox Sites in Human Cells

The following example provides a model system for assessing the ability of the pseudo-recombination sequences of the invention to promote genomic modification by site-specific insertion.

Figure 3:
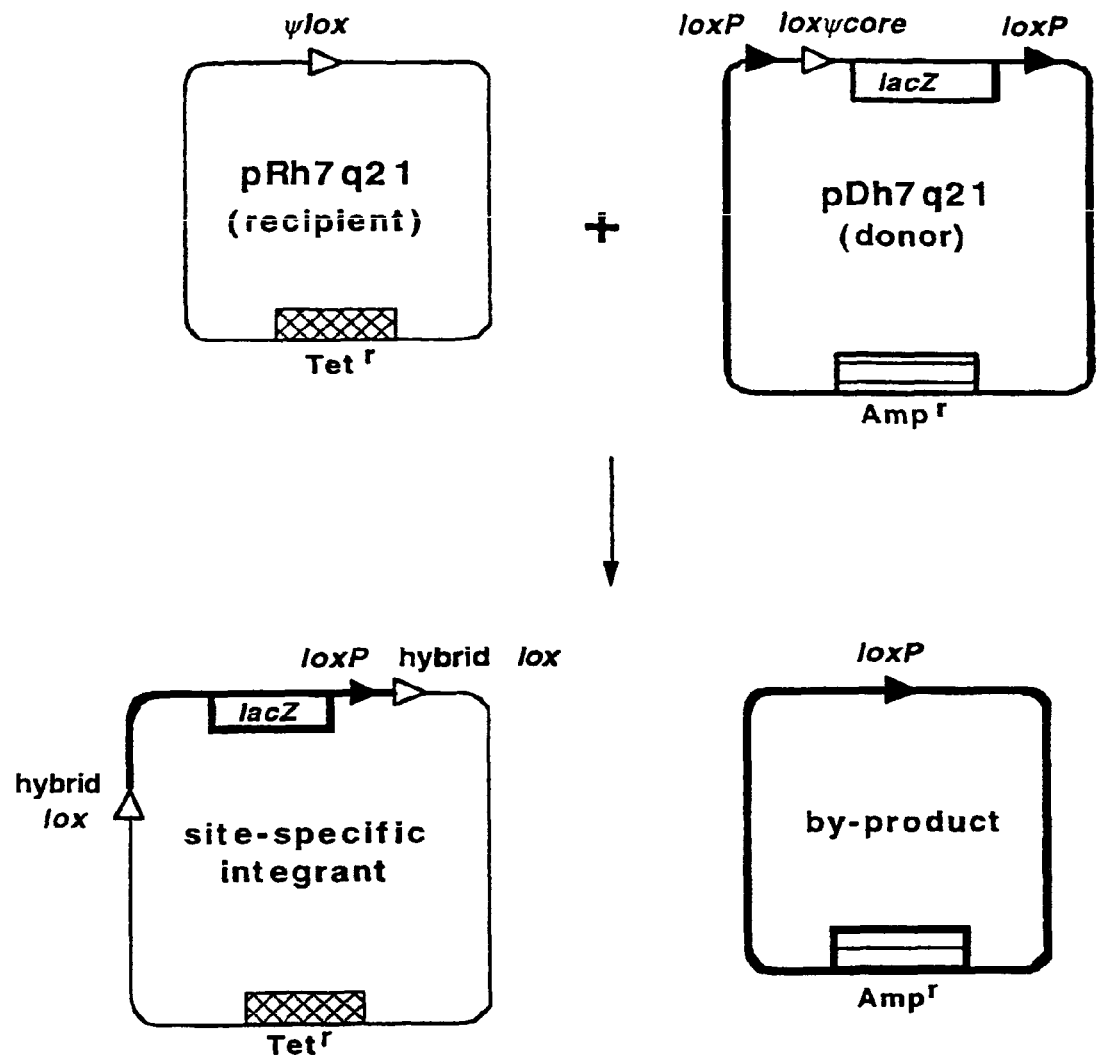
FIG. 3 is a diagram of plasmids used in a transient integration assay performed in human cells as described in the examples. pRh7q21 (upper left) was the recipient for an integration event and included the chromosomal ψlox h7q21 site (open triangle), as well as the gene for tetracycline resistance. Similar control plasmids bearing either no lox site or the wild-type loxP site were also constructed. pDh7q21 (upper right) was the donor plasmid for integration and included a lox site (open triangle, loxψcore) comprising the 8-bp core from ψlox h7q21 and the wild-type loxP palindromes. The plasmid also carried two wild-type loxP sites (dark triangles). In the presence of Cre, the plasmid origin of replication and the ampicillin resistance gene are excised, resulting in integrants that do not have two plasmid origins. This excised by-product is shown in the lower right. The site-specific integration product, bearing lacZ flanked by hybrid lox sites (shaded triangles) in a tetracycline resistant backbone, is shown at lower left. Parallel donor plasmids having, in place of ψlox h7q21, either no lox site or only wild-type loxP sites, were also constructed.

The ψlox site to be tested was placed on a plasmid having tetracycline resistance (FIG. 3, upper left). This plasmid represented the chromosome and was the recipient for integration events, A lox site having the wild-type loxP palindromes and the 8-bp core of ψlox h7q21 was placed next to the lacZ gene on a second plasmid, this one having ampicillin resistance (FIG. 3, upper right). This plasmid represented the incoming donor vector. These plasmids were constructed as follows: The plasmid pTM1 was generated by cloning a 155 base-pair AflIII-SnaBI fragment from pLitmus29 containing the multiple cloning site into a unique EcoRV site of pUC-Tet, a tetracycline resistant derivative of pUC19 (C.R. Sclimenti and M.P.C., unpublished). The lox sites of interest were then cloned into the BglII-XhoI site of this plasmid to generate the recipient plasmids for the integration assay (pRWT and pRh7q21).

The plasmid pLGWTLox[2] was used as a base for the construction of the donor plasmids used in the integration assay. pLGWTLox[2] was created by treating pWTLox[2] with EcoRI and subsequent religation to excise the CMV promoter and create a unique EcoRI site between one of the loxP sites and the lacZ gene. Complementary oligonucleotides containing the loxP-derived palindromes with the core derived from the ψlox h7q21, a marker enzyme site, and EcoRI half-sites at the ends were annealed and ligated into the unique EcoRI site of pLGWTLox$^2$ to generate the pDh7q21 donor plasmid for the transient integration assay.

To perform the assay, 50 ng of the tetracycline-resistant recipient plasmid and 1 µg of the ampicillin-resistant donor plasmid were co-transfected into human 293 cells with Lipofectamine along with 2 µg of the Cre expression vector pBS185-Kan. The transfected cells were treated with DNaseI 24 hours after transfection. After 72 hours in human cells, plasmid DNA was purified by Hirt extraction (Hirt, J. Mo. Biol. 26:365-369, 1967) and returned to the DH10B strain of E. coli for detection of integration events. Plasmids that underwent integration were tetracycline resistant and now also carried lacZ (FIG. 3, lower left). They thus gave rise to blue colonies when plated on LB medium containing tetracycline and X-gal and incubated overnight at 37° C. Plasmid DNA was purified from blue colonies, and those plasmids with the restriction pattern expected for integration were classified as integrants. Each blue colony was restreaked on LB plates containing X-gal and either ampicillin and methicillin, or tetracycline. One representative plasmid was sequenced in the relevant regions to document integration at lox sites. The integration frequency was calculated as the number of integrants divided by the total number of tetracycline-resistant colonies.

The integration assay was performed with recipients bearing the ψlox h7q21 site or controls having either the wild-type loxP site or no lox site, along with the corresponding donors. The integration frequency at the wild-type loxP site was 0.41%. Integration at the ψlox h7q21 site was readily detectable and occurred at a frequency of 0.12%. Experiments performed with either the recipient alone or the donor alone in the presence or absence of the Cre expression plasmid did not yield any integrants. Transfection of the recipient and the donor in the absence of the Cre expression plasmid also failed to yield any integrants. These results demonstrate that detectable site-specific integration occurs at a pseudo-lox site in the human cell environment.

A second type of shuttle vector system that can be used to model chromosomal integration utilizes modified autonomously replicating vectors such as those described in issued U.S. Pat. No. 5,707,830. These types of vectors replicate stably in human cells and have a very low endogenous mutation frequency (DuBridge, et al, Mol. Cell. Biol. 7:379-387, 1987). Thus, they provide better models for the chromosome than newly transfected plasmid DNA. One preferred shuttle vector may have EBNA-1 sequences, the EBV family of repeats, oriP or a human chromosomal ori, a bacterial origin of replication, and a pseudo-lox sequence and a marker gene such as one conferring hygromycin resistance. This vector is established in mammalian cells using antibiotic selection. The cells are transfected with a plasmid expressing Cre and a plasmid having a lox recombination sequence and a second marker gene, such as a gene for chloramphenicol resistance. The assay is performed as described above.

Example 4

In vitro Chromosomal Assay for Integration Efficiency

The following example evaluates the efficiency at which a heterologous nucleic acid sequence can be inserted into a chromosome at a particular pseudo-recombination site (integration efficiency) and the level of expression of a gene sequence inserted therein.

Bicistronic assay vectors are constructed containing, for example, a gene coding for hygromycin resistance under the control of the thymidine kinase promoter and a gene encoding the enzyme chloramphenicol acetyl transferase (CAT) under the control of the cytomegalovirus immediate early promoter (Wohlgemuth, et al, Gene Therapy 3:503-512, 1996). The former marker is used primarily to assess integration frequency while the latter marker is useful for sensitively assaying the level and duration of gene expression. The vector additionally carries a lox sequence containing the core of the pseudo-loxP sequence under evaluation.

The test plasmid is transfected into mammalian cells, such as 293S cells (human) or NIH3T3 cells (mouse), along with a Cre-expressing plasmid, such as one of those described above. The transfected cells are grown in the presence of hygromycin and the number of hygromycin resistant colonies scored as a measure of integration frequency. A number of antibiotic resistant colonies are propagated and analyzed by polymerase chain reaction (PCR) and Southern blotting to determine whether they have an integration event targeted to the correct ψlox site. CAT gene expression is measured as follows. Cell extracts are prepared by standard procedures and total protein of the extract is normalized for total protein concentration and assayed for CAT activity as described by Gorman, et al, Proc Natl Acad Sci USA 79:6777, 1982 or Wohlgemuth, supra.

Example 5

In vivo Assay for Integration

The following assay evaluates the ability of a recombination sequence to promote integration of a heterologous nucleic acid sequence into a genome in vivo.

The in vivo integration and expression of the CAT gene by employing the teaching of the invention is evaluated essentially as described by Zhu, et al, Science 261:209-211, 1993. Vectors, one containing a lox recombination sequence and CAT gene and one expressing Cre, are mixed with liposomes that have a net cationic charge, for example, containing N[1-(2,3-dioleyloxy) propyl]-N,N,N-trimethylammonium chloride (DOTMA) (Felgner, et al, Proc Natl Acad Sci USA 84:7413, 1987) and dioleoyl phosphatidylethanolamine (DOPE) in a 1:1 ratio. The ratio of DNA to liposomes is typically 1:1. The liposome/DNA mixture is typically injected into test mice in 200 µl of 5% dextrose in water intravenously through the tail vein.

At various time points, starting at 24 hours post-injection, test mice are sacrificed and various tissues harvested and homogenized. Cleared homogenates are assayed for CAT enzyme activity using a scintillation counting assay (Seed and Sheen, Gene 67:271-277, 1988) with the following modifications: 0.3 µCi of $^{14}$C-labeled chloramphenicol (55 mCi/mmol) is added to 200 nmol of acetyl coenzyme A for a final volume of 122 µl. CAT activity is expressed as either CAT enzyme/weight of tissue or as a function of milligrams of protein in each tissue extract. Tissue extracts are prepared by standard procedures and total protein determined using standard protocols (Bradford, Lowrie, and the like).

Example 6

Intramolecular Integration Assay for a Site-Specific Recombinase in E. coli

The following example describes a rapid assay to measure site-specific integration by a recombinase. This assay was used to measure integration of the wild-type type φC31 attB sequence into the wild-type φC31 attP sequence in the presence of the φC31 integrase. A similar assay can be used measure integration mediated by other recombinases of interest, such as the integrases of phages R4 and TP-901.

Figure 4A:
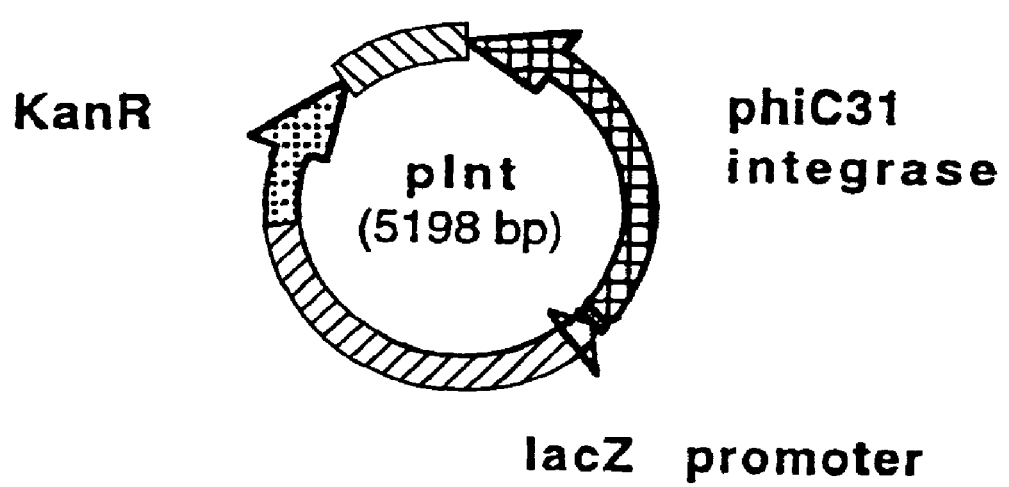
FIGS. 4A through 4E are schematic diagrams of representative plasmids used in demonstrating function of the φC31 integrase, as described in the examples.
Figure 4B:
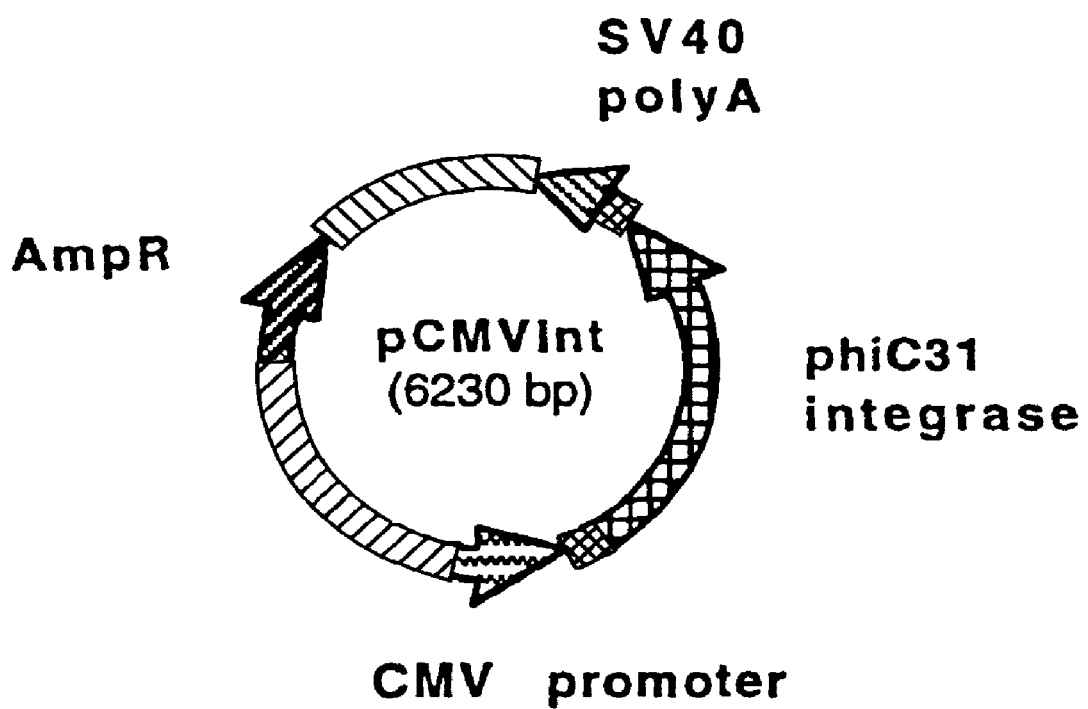

Integrase-expressing plasmids were constructed as follows. The φC31 integrase gene was amplified by the polverase chain reaction from the plasmid pIJ8600 containing the φC31 integrase and attP (M. Bibb, John Innes Institute, Norwich, U.K.) with the following primers: 5'GAAC-TAGTCGTAGGGTCGCCGACATGACAC3' (SEQ ID NO: 6) and 5'GTGGATCCGGGTGTCTCGCTACGCCGCTAC3' (SEQ ID NO: 7). The PCR product was ligated into linear pCR2.1 (Invitrogen, Carlsbad, Calif.) at the T overhang to make the plasmid pTA-Int. The lacZ gene was removed from pCMVSPORTβGal (Life Technologies, Grand Island, N.Y.) by digestion with the restriction enzymes BamHI and SpeI, and replaced by the integrase gene from pTA-Int with BamHI and SpeI compatible ends, creating the plasmid, pCMVInt (FIG. 4B), which expresses φC31 integrase in mammalian cells under control of the cytomegalovirus immediate early promoter.

The integrase gene was subsequently removed from pCM-VSPORTInt by digestion with BamHI and PstI and ligated into pACYC 177 resistances ampicillin and kanamycin) (S. Cohen, Stanford University, Stanford, Calif.) that had also been treated with BamHI and PstI, removing part of the ampicillin resistance gene. Finally, the lacZ promoter was removed from pBCSK+ (Stratagene, La Jolla, Calif.) by digestion with Sad and SapI. The integrase-containing pACYC plasmid was digested with PstI and SacI, and the lacZ promoter was inserted upstream of the integrase gene with a linker (5 GCTCGGCCA-AAAAGGCCTGCA3' (SEQ ID NO: 8), 5'GGCCTTTTTGGCCG3' (SEQ ID NO: 9)), creating the plasmid, pInt (FIG. 4A), expressing the φC31 integrase under control of the lacZ promoter.

Figure 4C:
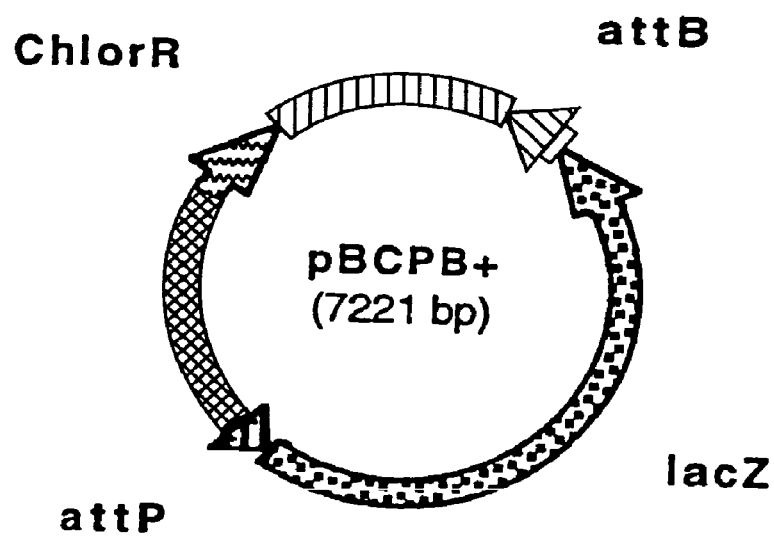

The intramolecular integration assay plasmid was constructed as follows. The bacterial attachment site for φC31 (attB) was amplified by PCR from *Streptomyces lividans* genomic DNA (S. Cohen, Stanford University, Stanford, Calif.) with the primers: 5'CAGGTACCGTCGACGATG-TAGGTCACGGTC3' (SEQ ID NO: 10) and 5'GTCGACAT-GCCCGCCGTGACCG3' (SEQ ID NO: 11). This attB fragment was ligated into linear pCR2.1 at the T overhang sites to create the plasmid pTA-attB containing a 285 by attB region. The phage attachment site (attP) was amplified by PCR from pIJ8600 with the primers 5'CGACTAGTACTGACGGACA-CACCGAAA3' (SEQ ID NO: 12), 5'GTAC-TAGTCGCGCTCGCGCGACTGACG3' (SEQ ID NO: 13) and ligated into linear pCR2.1 at the T overhang sites to create the plasmid pTA-attP, containing a 221 by attP region. The lacZa was removed from pBCSK+ by digestion with PvuI and KpnI, treatment with T4 polymerase, and religation. The full length lacZ gene from pCMVSPORTBGa1 was removed by digestion with SpeI and HindIII and cloned into the SpeI and HindIII sites of the lacZa deficient pBCSK+ to make pBCβ-Gal. The attP was then removed from pTA-attP by SpeI digestion and cloned into the SpeI site of pBCβGal. The attB was then removed from pTA-attB by SalI digestion and cloned into the SalI site of the attP containing pBCβGal, to create the assay plasmid pBCBP+ (FIG. 4C), in which the TTG cores of the att sites are in the same orientation. In addition, a control plasmid, pBCPB−, in which the att sites were in opposite orientations, was also constructed.

The pInt plasmid was then transformed into DH10B bacteria, grown under kanamycin selection, and made electrocompetent by a standard protocol. The resulting electrocompetent DHInt cells were used in the bacterial intramolecular integration assay, conducted as follows. 200 ng of the assay plasmid of choice was electroporated into DHInt cells, allowed to recover for one hour, spread on plates containing chloramphenicol and Xgal, and grown at 37° C. If an intramolecular integration event occurs, the lacZ gene located between the attB and attP sites will be excised, and a resulting colony will be white. The frequency of intramolecular integration was therefore calculated as the number of white colonies divided by the total number of colonies.

When this assay was carried out in DHInt bacteria using pBCPB+, all colonies were white, indicating efficient integration. Thousands of colonies were assayed for each plasmid tested. The same plasmid produced only blue colonies in DH10B bacteria, in the absence of the integrase gene. These results verify that the assay plasmid carried functional attB and attP sites and that the φC31 integrase functioned efficiently in *E. coli* with no added co-factors. In contrast, the plasmid pBCPB−, which carried the att sites in inverted orientation, resulted in blue colonies, because the lacZ gene was merely inverted, not excised, by the integration reaction. The assay plasmid with no att sites, pECSK-βgal, also yielded only blue colonies in DHInt cells. Restriction enzyme digestion of plasmid DNA purified from a representative number of white colonies verified that the intramolecular integration reaction occurred as expected and resulted in deletion of lacZ between the attB and attP sites.

Example 7

Intramolecular Integration Assay in Mammalian Cells

The following example demonstrates the ability of phage φC31 integrase to integrate sequences site-specifically and efficiently in a mammalian cell environment.

To perform the intramolecular integration assay in human cells, the same pBCBP+ plasmid was used as in the bacterial assay of Example 6. The pCMVInt plasmid was substituted for pInt to ensure expression of φC31 integrase in mammalian cells. Subconfluent (60-80%) 60 mm plates of human 293 cells grown in DMEM supplemented with 9% fetal bovine serum and 1% penicillin/streptomycin were transfected with lipofectamine (Life Technologies) at a ratio of 6 μg lipofectamine per μg of DNA. Experiments were performed with 100 ng of the assay plasmid of interest and 2 μg of pCMVInt. Controls performed in each experiment included no DNA, pCMVInt only, pSCSK-βgal (assay plasmid with no att sites), pBCSK-βgal+pCMVInt, and pBCPβ+ alone.

Twenty-four hours after transfection, the medium was supplemented with 50 Units/ml of DNaseI to reduce the background of untransfected DNA. Three days after transfection, the cells were harvested and low molecular weight DNA was recovered by using the Hirt procedure (Hirt, J. Mo. Biol. 26:365-369, 1967). A portion of this DNA was electroporated into competent DH10B *E. coli* cells and spread on plates containing chloramphenicol and Xgal to select only for the assay plasmid. The intramolecular integration frequency was determined to be the number of white colonies divided by the total number of colonies.

Using this assay system in mammalian cells, the φC31 integrase was shown to catalyze recombination between the full-length attB and attP sites of pBCBP+ at a frequency of 50.6% (mean of 16 experiments, standard error=2.32%). This frequency is likely to be an underestimate as plasmid DNA that never came in contact with the φC31 integrase was probably present, despite efforts to remove untransfected DNA with DNaseI. It is clear that the φC31 integrase catalyzes efficient site-specific integration in mammalian cells.

To verify site-specific recombination, 96 white colonies were picked and plasmid DNA was prepared and examined by restriction digestion. Of these, 97% contained a plasmid that represented the expected site-specific recombinant. The remaining colonies contained plasmids that carried large rearrangements that disrupted lacz. The low frequency rearrangement of transfected plasmids was observed with all plasmids, with and without integrase and att sites, and can be attributed to transfection-associated mutation of newly introduced DNA.

Example 8

Determination of the Minimal Sizes of Recombination Sequences

The following example describes the process for determining the minimal sequences needed for recognition and recombination by a site-specific recombinase. This process was used to determine the minimal wild-type attB and attP sequences functionally recognized by the φC31 integrase in bacterial and mammalian cell environments. A similar process can be used to identify the minimal sequences recognized by other recombinases of interest, such as the integrases of phages R4 and TP-901. The minimal attB and attP sequences can then be used to identify pseudo-recombination sequences, for example as described above for the Cre-lox system.

Prior to this study, the minimal sizes for the φC31 attachment sites, attB and attP, had not been determined. The attB site had been localized to approximately 280 basepairs and the attP region had been localized to 86 basepairs (Thorpe and Smith, Proc. Natl. Acad. Sci. USA, 1998). The intramolecular integration assay described in Example 6 was used to determine the minimal functional sizes for these att sites. Short double-stranded adaptor molecules containing att sites of various lengths were created by annealing single-stranded oligonucleotides. These shorter sites were used to replace the full-length att sites in the pBCPB+assay plasmid, and recombination efficiencies were determined by electroporation into E. coli.

Figure 5:
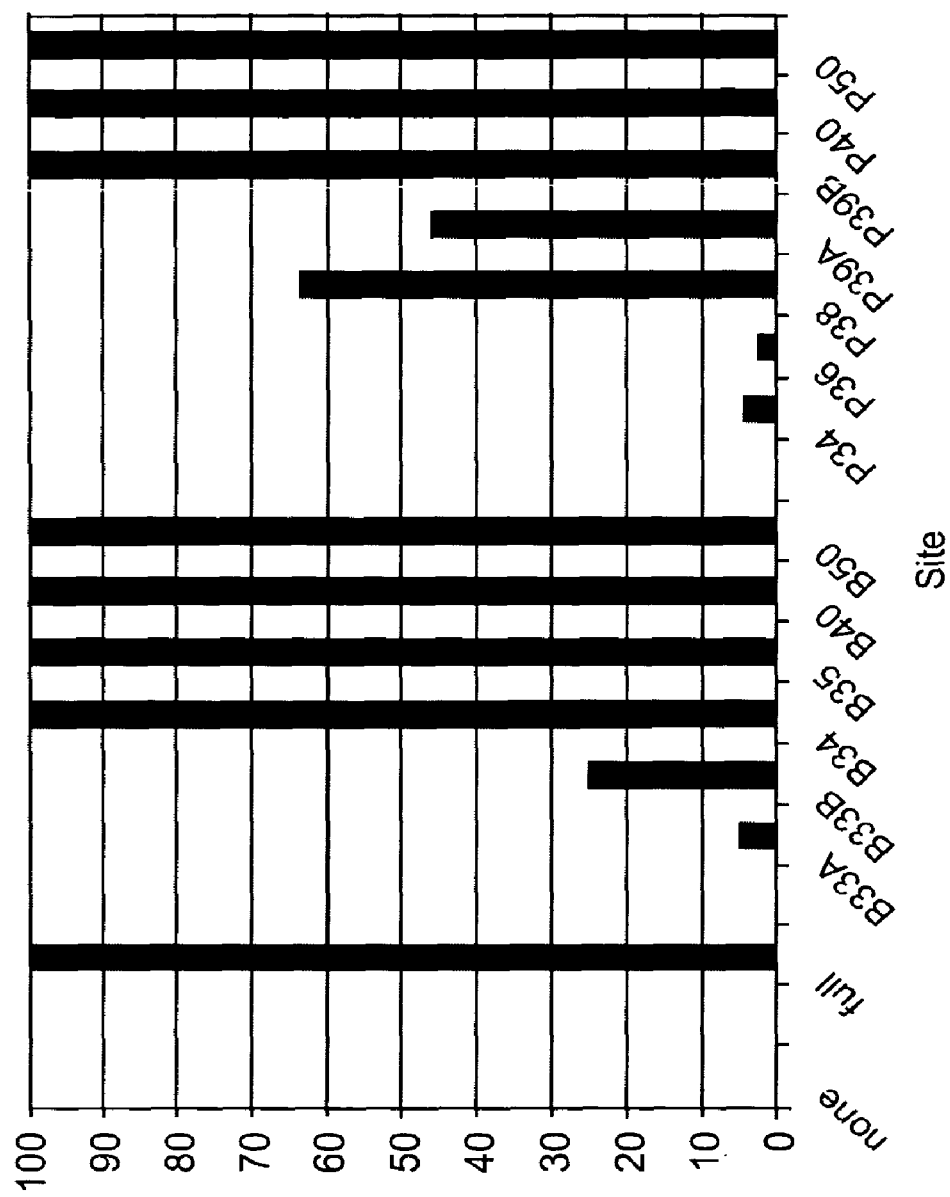
FIG. 5 shows along the vertical axis the percent recombination obtained in the intramolecular integration assay in E. coli, described in Example 6, when various shortened versions of φC31 attB (left) and attP (right) were tested. The name of each site tested corresponds to the length of the att site in basepairs. The A and B of B33 indicate sites where the reduction of the site length from 34-bp to 33-bp occurred at the left or right ends of the site, respectively. Similar nomenclature is used for P39A and P39B. Full refers to the full length attB.

To determine the minimal function size of attB, the 278-basepair full-length attB surrounded by BamHI and HindIII sites was removed. This fragment was replaced by the series of synthetic shorter sites having ends permitting their orientation-appropriate cloning into pBCBP+. The resulting plasmids were electroporated into DHInt E. coli a cells and recombinants were scored as white colonies, as described in Example 6 above. FIG. 5 (left side) shows the results of these experiments. AttB sites of 50, 40, 35, and 34 basepairs all provided full recombination function, i.e. they functioned at 100% of the efficiency of the full-length attB. Reduction of the site to 33 basepairs produced a marked decrease in recombination activity. Therefore, 34 basepairs was determined to be the minimal function size of attB.

Once attB was determined to be 34 basepairs long, attP was subjected to a similar set of reductions. The reduced attP sites were assayed on a plasmid carrying attB34 rather than full-length attB. To perform these experiments, the full-length attP surrounded by SacII and SpeI sites was replaced with a series of synthetic annealed oligonucleotides bearing ends permitting their correct orientation-specific cloning into pBCPB+-attB34. FIG. 5 (right side) depicts the results of these experiments. The function of attP dropped off as its size was reduced from 40 to 36 basepairs. The DNA sequence revealed that the 38 basepair site encompassed the major inverted repeat evident in attP. However, it was apparent from this data that the next two outermost basepairs conveyed some function (P39A&B). From this analysis, the minimal size of attP was determined to be 39 basepairs.

To determine the frequency at which the reduced att sites function in mammalian cells, the same panel of plasmids was analyzed by using the intramolecular integration assay described in Example 7. Each of the assay plasmids was transfected into human 293 cells along with pCMVInt. After 72 hours in the mammalian cells, the plasmid DNA was purified by the method of Hirt (Hirt, J. Mo. Biol. 26:365-369, 1967) and transformed into DH10B E. coli cells for scoring of recombinants. The results of these experiments showed that minimal sizes for attB and attP similar to those determined in E. coli also applied in mammalian cells. Approximately 60-90% of the efficiency of the full-length att sites was achieved with the same reduced att sequences that worked at 100% efficiency in E. coli, likely because the overall reaction is somewhat less efficient in the mammalian cell environment.

These experiments to determine the minimal sizes of attB and attP provided the information that these recombination sites had sizes of 34 and 39 basepairs, respectively. These sizes are similar to that of the 34-basepair loxP site. A recombination site of this size will possess active pseudo recombination sites in large genomes, such as those of mammals and most plants. Thus, it is statistically expected that the pseudo recombination sites for the φC31 integrase will occur in these genomes. These pseudo recombination sites represent targets for chromosome engineering.

Example 9

Determination of the Amount of Heterogeneity Tolerated in the Core Sequence of a Recombinase Site The amount of heterogeneity tolerated in the 3-bp core sequence of the attB and attP sequences recognized by the φC31 integrase was determined. Similar methods can be used to determine the amount of core heterogeneity tolerated in the cores of other recombinases of interest, such as the integrases of phages R4 and TP-901.

The φC31 integrase catalyzes recombination between attB and attP sites. These sites have minimal functional lengths of 34 and 39 basepairs, respectively. While largely distinct in sequence, attB and attP share a three basepair common core sequence, TTG, that includes the crossover region. In the case of the 8-basepair core region of the loxP site targeted by Cre recombinase, it has been found that its sequence is largely unimportant, as long as it matches between the two recombining sites. To determine if this behavior applied to the core region of the attB and attP sites of the φC31 integrase, the effects of mutations within this core region were examined.

A panel of plasmids was generated in which either attB, attP, or both sites were altered with a specific single base change. These changes were then assayed with the intramolecular integration assay in E. coli described in Example 6. A recombination event results in excision of the lacZ gene located between the att sites. Thus, when an assay plasmid is transformed into bacteria expressing φC31 integrase, a site-specific recombination event is scored as a white colony.

The TTG core was mutated in each position individually to all other base possibilities. The effects of these mutations in attB were investigated when paired with a wild-type attP. Conversely, the effects of a mutant attP paired with a wild-type attB were measured. By combining attB and attP sites that contained identical mutations, it was determined whether the core region needed to only match to be effective in recombination.

Figure 6:
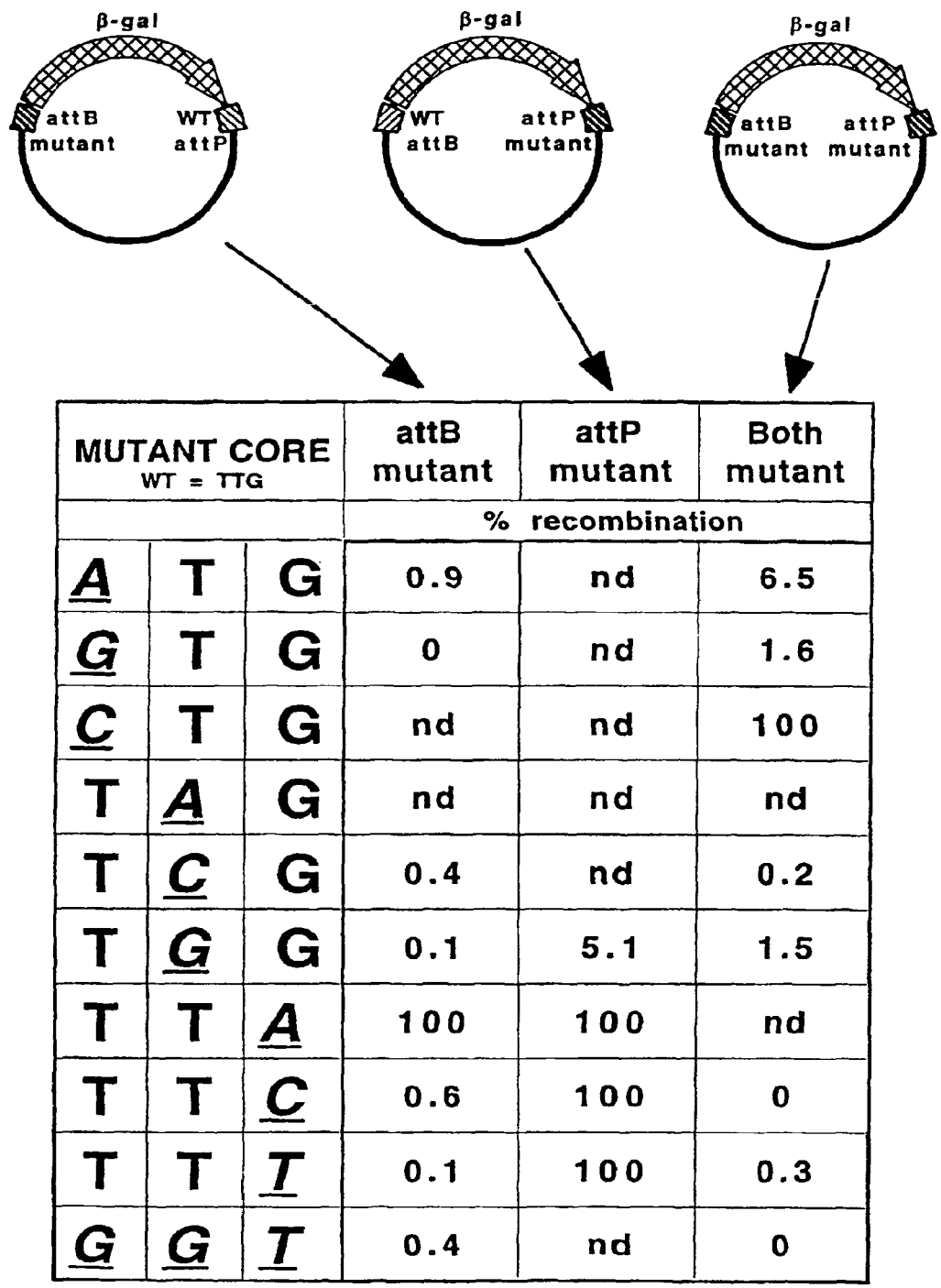
FIG. 6 shows the percent recombination obtained in the intramolecular integration assay performed in E. coli when various substitutions in the attB and/or attP cores were made. The first column shows the recombination frequency when attB bears the mutant sequence shown and attP remains wild-type, the second column shows the recombination frequency when attD bears the mutant sequence, while the third column shows the recombination frequency when both attB and attP bear the mutant core sequence shown. nd=not done. As the figure indicates, most changes in the core region are not well tolerated.

To carry out these experiments, oligonucleotides bearing the mutations to be tested were synthesized in the context of attB34 or attP40 (see Example 8). The mutant oligonucleotides were annealed and cloned into the chloramphenicol-resistant intramolecular integration assay vector pBCBP+ to replace the wild-type attB or attP, as in Example 8. Individual plasmids containing the mutation of interest were assayed for recombination in *E. coli* strain DHInt, which carries the kanamycin-resistant integrase expression plasmid pint, described in Example 6. Assay plasmid DNA (2 ng) was electroporated into DHInt, and after a 1 hour recovery period at 37° C. in rich media, the transformations were plated on LB agar containing 25 mg/ml chloramphenicol, 60 mg/ml kanamycin, and 50 mg/ml X-gal. The plates were incubated overnight (16-18 hours) at 37° C., after which blue and white colonies were counted. The recombination fraction was expressed as the percentage of white colonies out of total colonies. The results of these experiments are shown in FIG. 6.

The first and third positions of the core showed some flexibility, while the center position did not. The first position appeared to tolerate only pyrimidines; the CTG double mutant worked well. The third position of attP could be changed to any base, and to the other purine for attB. Overall, the pattern of base substitutions tolerated in the recognition sites for the φC31 integrase more closely resembled the degree of tolerance for substitutions typical of the outer palindromes, rather than the core, of the loxP site. Thus, unlike the situation in the Cre-loxP system, the φC31 integrase has strong base preferences within the cores of its attB and attP recombination sites, and merely matching any two three-basepair core sequences will not suffice to generate efficient recombination in this system.

Example 10

Bimolecular Integration Assay Into a Model Chromosome in Mammalian Cells

The following example demonstrates the ability of phage φC31 integrase to integrate sequences site-specifically and efficiently into a model chromosome in a mammalian cell environment.

Example 7 demonstrated that the φC31 integrase efficiently catalyzed site-specific intramolecular integration in mammalian cells. The next step was to show that the integrase could catalyze efficient site-specific integration of exogenous DNA into mammalian chromosomes in cell culture. EBV-based plasmids provide easy and useful models for chromosomes. EBV vectors exist in the nucleus, replicate in synchrony with the chromosomes, and bear chromatin indistinguishable from that of the chromosomes. They can be easily purified from cells and transformed into *E. coli* for rapid scoring of integration events. Thus they have great utility in characterization of the integration reaction in human cells.

In these experiments, a kanamycin-resistant EBV plasmid was equipped with an attB site and established in human 293 cells to create a stable attB-containing human cell line. An ampicillin-resistant plasmid carrying attP and lacz was then co-transfected into the attB cell line, along with a plasmid expressing the φC31 integrase. To assay for integration products, after three days plasmid DNA was extracted and transformed into bacteria. Blue colonies that grew on plates containing kanamycin, ampicillin, and Xgal were scored integrants, while total colony number could be obtained by plating on kanamycin alone.

Figure 4D:
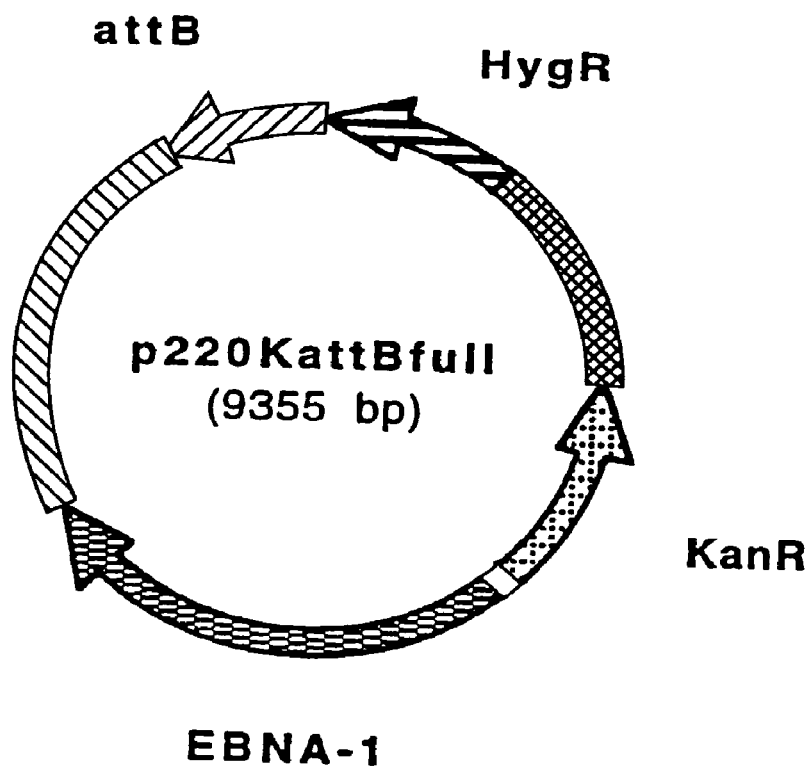

The attB and attP plasmids needed for this study were constructed as follows. The target EBV based plasmids were based on p220.2 (DuBridge et all 1987). The control plasmid p220K was made by inserting the kanamycin resistance gene from the Kan-resistant Genblock (Amersham Pharmacia, Piscataway, N.J.) into the XmnI site of the ampicillin resistance gene of p220.2. To make attB-containing p220 plasmids, the ampicillin resistance gene of p220.2 was removed by digestion with BspHI. The kanamycin resistance gene described above was isolated by digestion with PstI, and cloned into amp-220.2 with BspHI-PstI linkers (5'CATGAG-GCCWGGCCTGCA3' (SEQ ID NO: 14) and 5'GGC-CTTTTTGGCCT3' (SEQ ID NO: 15)) to create the plasmid p220K. The full length attB was removed from the plasmid pTA-attB (Example 6) by SalI digestion and cloned into the SalI site of p220K, creating the plasmid p220KattBfull (FIG. 4D). The 35 base pair attB was cloned into the SalI and BamHI sites of p220K by using the oligonucleotides, 5'gatc-cgatatcgcgcccggggagcccaagggcacgccctggcaccg3' (SEQ ID NO: 16) and 5'tcgacggtgccagggcgtgccct-tgggctccccgggcgcgatatcg3' (SEQ ID NO: 17), creating the plasmid p220KattB35.

These EBV plasmids, p220K, p220KattBfull, and p220KattB35, were established in human 293 cells as follows. 293 cells were grown in DMEM containing 9% fetal bovine serum and 1% penicillin/streptomycin to −70% confluency in a 100 mm plates. 8 μg of p220KattBfull, p220KattB35, or the control p220K were introduced by transfection with lipofectamine according to the manufacturer's protocol. At 24 hours post-transfection, the cells were split 1:4, and at 48 hours post-transfection hygromycin selection (350 μg/ml) was begun. 11 to 14 days after starting selection the cells were expanded and frozen down.

Figure 4E:
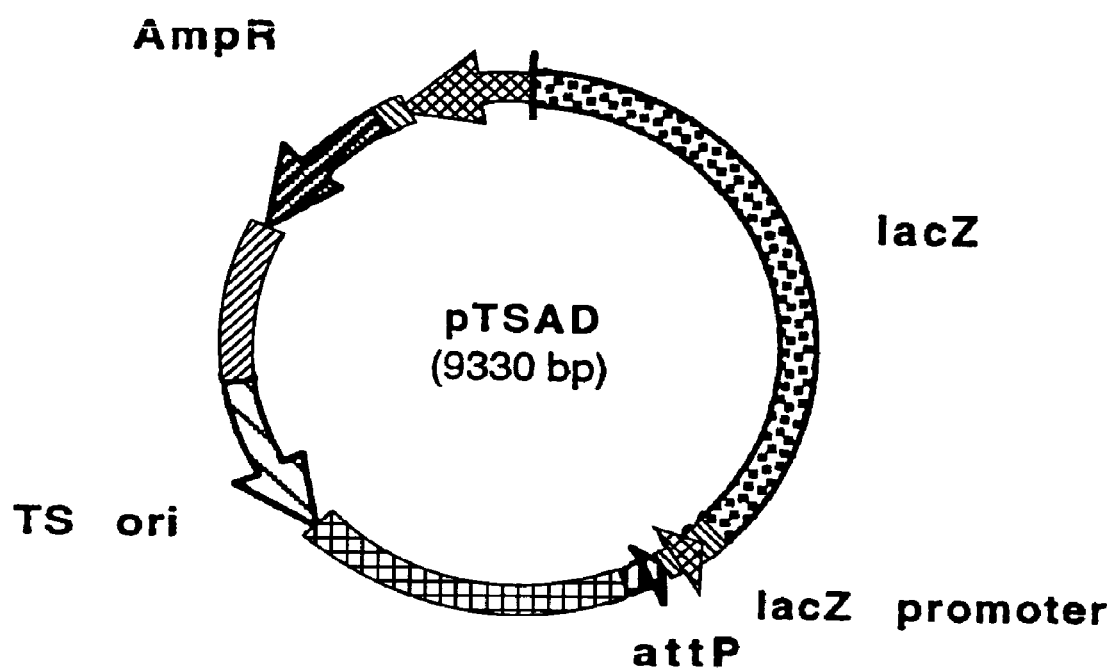

The attP-containing plasmid pTSAD (FIG. 4E) was constructed as follows. A multiple cloning site (oligos: 5'AAT-TACCGCGGGGCGCGCCGTTTAAACGCAT-GCCAATTGGGCCGGCCG3' (SEQ ID NO: 18) and 5'AATTCGGCCGGCCCAATTGGCATGCGTT-TAAACGGCGCGCCCCGCGGT3' (SEQ ID NO: 19)) was cloned into the EcoRI site of the plasmid pWTLox² (Example.2) upstream of lacZ, regenerating one EcoR1 site. The attP site was removed from the plasmid pTAattP (Example 6) by digestion with EcoRI and cloned into the regenerated EcoRI site of pWTLox² to create the plasmid pES 1. The lacZ promoter was removed from pBCSK+ by digestion with PvuII and SacII and cloned into pES1 which had been digested with PmeI and SacII. The region containing attP, the lacZ promoter, and the lacZ gene was removed by digestion with BamHI and BglII and cloned into the BamHI site of pTSA30 (Gregory Phillips, Iowa State University, Ames, Iowa) to create the donor plasmid pTSAD. pTSA30 and its pTSAD derivative are temperature sensitive for plasmid replication in *E.coli*.

To perform the integration assay, EBV plasmid-containing cells were grown to confluency in DMEM containing 9% fetal bovine serum, 1% penicillin/streptomycin, and 200 μg/ml hygromycin in 10 cm plates. These plates were split into eight 60 mm plates and grown in the above medium without hygromycin for 24-48 hours, until they were approximately 60-80% confluent. pCMVInt (Example 7, FIG. 4B) and pTSAD were transfected in equimolar amounts (10 μg total DNA) using 50 μl Superfect (Qiagen, Valencia, Calif.) according to the manufacturer's protocol. As controls, no DNA, 4 µg pCMVInt, or 6 µg pTSAD were cotransfected with salmon sperm DNA (to 10 µg). In addition, an equimolar amount of a plasmid encoding the green fluorescent protein (a derivative of pEGFP-cl, Clonetech, Palo Alto, Calif.) with salmon sperm DNA to 10 µg was transfected in parallel into the EBV plasmid-containing cells to monitor transfection efficiency.

2.5-3 hours after transfection, the Superfect was removed from the cells and replaced with serum-containing medium. Cells were fed with medium containing serum and 50 U/ml 24 hours after transfection and harvested 72 hours after transfection. Low molecular weight DNA was purified by Hirt extraction (Hirt, J. Mo. Biol. 26:365-369, 1967) and transformed into DH102 *E. coli* by electroporation. Also, 24 hours after transfection, transfection efficiency was measured by counting the green fluorescent protein-expressing cells relative to the total number of cells. The transfection efficiencies typically ranged from 6-18%. Because untransfected cells would have no opportunity to undergo integration but would still contribute EBV plasmids to the bacterial assay in the form of white colonies, the transfection efficiency was needed to obtain the correct the integration frequency.

In a typical experiment, 15 µl of a transformation was spread on each of three plates containing kanamycin, Xgal, and IPTG, while 150 µl of the same transformation was spread on each of three plates containing ampicillin, kanamycin, Xgal, and IPTG. The bacteria were grown overnight at 42° C. for approximately 16 h. The elevated temperature prevented replication of pTSAD, which has a temperature-sensitive plasmid origin of replication. Integrants were scored as the blue colonies on the plates containing both kanamycin and ampicillin. Integration frequency was calculated as the number of blue colonies on kanamycin and ampicillin plates divided by the total number of colonies on kanamycin plates X 10 for each set of transfections. Raw numbers for integration frequency were divided by transfection efficiency to obtain accurate values for integration frequency.

FIG. 7 lists the integration frequencies obtained with each of the EBV plasmids and the negative controls. Each line of the figure represents a minimum of three separate transfections. For p220K, which lacks the attB site, a negligible frequency of blue colonies was detected. Upon analysis, these plasmids were not integrants, but rather homologous recombination events that occurred through common amp sequences on the two plasmids. For p220KattB35, carrying a minimally sized attB, a significant number of blue colonies were detected. When corrected for the transfection efficiency in these experiments, the integration frequency was 1.7%. For p220KattBfull, the integration frequency was even higher, at 7.5%. This increase presumably reflects a favorable sequence context for the full attB site compared to the reduced site. Controls in which pCMVInt, pTSAD, and each of the EBV plasmids, p220K, p220KattBfull, and p220KattB35 were co-transformed directly into *E. coli* yielded negligible numbers of blue colonies (0.002% or less). These controls confirmed that the high frequency integration events scored above occurred in human cells, not in *E. coli*.

The integration frequency into an attB site located on an EBV plasmid is impressively high and several orders of magnitude higher than the frequencies of random integration or homologous recombination, highlighting the utility of this invention. Furthermore, the integrants are site-specific, as indicated by restriction mapping of more than 160 of the blue colonies from the experiments with p220KattB35 and p220KattBfull. In addition, two integrants each, from the experiments with p220Katt35 and p220Kattfull, were analyzed at the DNA sequence level across the junctions of the integration site, confirming that exact site-specific integration occurred between attB and attP. FIG. 7 indicates that, as expected, the reaction requires the presence of both the integrase gene (pCMVInt) and the attP target site (pTSAD). Because EBV vectors are nuclear, chromatinized mini-chromosomes, the high integration frequency obtained in this system is predictive of the expected integration frequencies into att sites located on the chromosomes.

Example 11

Assay for Integration Into the Chromosomes of Mammalian Cells

The following example describes methods used to demonstrate the ability of phage φC31 integrase to site-specifically integrate sequences into mammalian chromosomes.

Cell lines carrying the wild-type φC31 attB site are prepared by transfecting human 293 cells with Lipofectamine and a plasmid carrying the attB sequence and the hygromycin resistance gene. The cells are grown in DMEM containing hygromycin and resistant colonies propagated to mass culture. Integration of the attB sequence is verified by Southern blot analysis using plasmid sequences as probes. These cell lines are then transfected with Lipofectamine and a plasmid containing the attP sequence and a neomycin/G418 resistance gene and a plasmid expressing the φC31 integrase gene under control of the CMV promoter. The G418 antibiotic is added to the DMEM growth medium approximately 48 hours after transfection. Selection is maintained for approximately ten days, after which the number of colonies is scored.

Higher numbers of neomycin resistant colonies are seen in cells co-transfected with the φC31 integrase-expressing plasmid than in cells that do not receive the integrase. Likewise, higher numbers of neomycin-resistant colonies are obtained in cells lines carrying attB compared to the parent 293 cell line lacking attB. These results suggest that the φC31 integrase enzyme can catalyze the integration of heterologous sequences into a mammalian genome, both at an integrated attB sequence and at endogenous pseudo-recombination sequences.

Similar experiments can be conducted using cell lines carrying an integrated attP hygromycin-resistant plasmid, followed by transfection with a neomycin-resistant attB plasmid, to demonstrate integration into the integrated wild-type attP and attP pseudo-sites. Furthermore, similar experiments can be conducted in other cell types, such as those derived from other mammalian species or from plants, to test integration activity in these cellular backgrounds.

While the foregoing has been with reference to particular embodiments of the invention, it will be appreciated by those skilled in the art that changes in these embodiments may be made without departing from the principles and spirit of the invention, the scope of which is defined by the appended claims.

What is claimed is:

1. A method of integrating a nucleic acid into a genome of a fibroblast cell in vitro, comprising:

introducing into said fibroblast cell in vitro (i) an expression cassette comprising a polynucleotide encoding a φC31 phage recombinase; and (ii) a targeting vector comprising a nucleic acid and a single φC31 vector attachment site; and maintaining said cell under conditions sufficient for said targeting vector to integrate into an endogenous target site of said genome by a recombination event mediated by said φC31 phage recombinase.

2. The method according to claim 1, wherein said fibroblast cell is derived from a human subject.

3. The method according to claim 1, wherein said nucleic acid comprises a eukaryotic coding sequence.

4. The method according to claim 3, wherein said coding sequence encodes a polypeptide.

5. The method according to claim 3, wherein said coding sequence encodes an RNA molecule.

6. The method according to claim 3, wherein said coding sequence is present in an expression cassette.

7. A method comprising:
introducing into a genome of a fibroblast cell in vitro (i) an expression cassette comprising a polynucleotide encoding a φC31 phage recombinase; and (ii) a targeting vector comprising a nucleic acid and a single φC31 vector attachment site;
maintaining said cell under conditions sufficient for said targeting vector to integrate into an endogenous target site of said genome by a recombination event mediated by said φC31 phage recombinase; and
locally administering said cell to a human subject following integration of said nucleic acid into said genome of said cell.

8. The method according to claim 1, wherein said vector attachment site is a bacterial genomic recombination site (attB), a phage genomic recombination site (attP), a pseudo bacterial genomic recombination site (pseudo-attB), or a pseudo phage genomic recombination site (pseudo-attP).

* * * * *